(12) United States Patent
Le et al.

(10) Patent No.: US 6,555,563 B1
(45) Date of Patent: Apr. 29, 2003

(54) HETEROARYL SUBSTITUTED AMIDINYL AND IMIDAZOLYL COMPOUNDS AND METHODS EMPLOYING SAME FOR THE TREATMENT OF INFLAMMATION

(75) Inventors: Van-Duc Le, Albany, NY (US); Jean-Frédérick Salazar, San Diego, CA (US)

(73) Assignee: Medinox, Inc., San Diego, CA (US)

( * ) Notice: Subject to any disclaimer, the term of this patent is extended or adjusted under 35 U.S.C. 154(b) by 0 days.

(21) Appl. No.: 09/991,366

(22) Filed: Nov. 16, 2001

(51) Int. Cl.$^7$ ............................................. C07D 417/04
(52) U.S. Cl. ....................... 514/363; 514/364; 548/137; 548/145
(58) Field of Search ................................ 548/137, 145; 514/363, 364

(56) References Cited

U.S. PATENT DOCUMENTS

| | | | |
|---|---|---|---|
| 4,160,452 A | 7/1979 | Theeuwes | 128/260 |
| 4,256,108 A | 3/1981 | Theeuwes | 128/260 |
| 4,265,874 A | 5/1981 | Bonsen et al. | 424/15 |
| 5,510,361 A | 4/1996 | Scherz et al. | 514/378 |
| 5,616,601 A | 4/1997 | Khanna et al. | 514/399 |

FOREIGN PATENT DOCUMENTS

| | | | |
|---|---|---|---|
| WO | WO 9727181 | * | 7/1997 |

OTHER PUBLICATIONS

Faidallah HM, Mokhtar HM, Moustafa JM, et al. Triazole–pyrazole compounds with possible biological activity. Part 1 synthesis and spectra. Pak J Sci Ind Res. 1992;35:213–20. (abstract only).*

Ashry et al., "Acyclic C–Nucleoside Analogs of the Type of 5–C–Polyhydroxyalkyl–1,3,4,–thiadiazoles," Bull. Chem. Soc. Japan, 60, 3405–3409, 1987.

Battistini et al., "Cox–1 and Cox–2: Toward the Development of More Selective NSAIDs," DN&P, 7(8), 501–512, 1994.

Clemett et al., "Celecoxib: A Review of its Use in Osteoarthritis, Rheumatoid Arthritis and Acute Pain," Drugs, 59(4), 957–980, 2000.

Griswold et al., "Constitutive Cyclooxygenase (COX–1) and Inducible Cyclooxygenase (COX–2):Rationale for Selective Inhibition and Progress to Date," Medicinal Research Reviews, 16(2), 181–206, 1996.

Koguro et al., "Novel Synthesis of 5–Substituted Tetrazoles from Nitriles," Synthesis, 910–914, 1998.

Lawrence et al., "Estimates of the Prevalence of Arthritis and Selected Musculoskeletal Disorders in the United States," Arthritis & Rheumatism, 41(5), 778–799, 1998.

Le et al., "From Tetrazoles via Hydrazonoyl Chlorides to 1,3,4–Thiadiazole Oligomers," Tetrahedron Letters, 41, 9407–9411, 2000.

Mullican et al., "Design of 5–(3, 5–Di–tert–butyl–4–hydroxyphenyl)–1,3,4–thiadiazoles,1,3, 4–oxadiazoles, and –1,2,4–thiazoles as Orally–Active, Non-ulcerogenic Antiinflammatory Agents," J.Med.Chem, 36, 1090–1099, 1993.

Singh et al., "Epidemiology of NSAID Induced Gastrointestinal Complications," Journal of Rheumatology, 26, Supplement 56, 18–24, 1999.

Song et al., "Synthesis, Structure–Activity Relationships, and in Vivo Evaluations of Substituted Di–tert–butyl– Phenols as a Novel Class of Potent, Selective, and Orally Active Cyclooxygenase–2 Inhibitors 2. 1,3,4– and 1,2,4–Thiadiazole Series," J. Med. Chem., 42, 1161–1169, 1999.

Vane, "Towards a Better Aspirin," Nature, 367, 215–216, 1994.

* cited by examiner

Primary Examiner—Joseph K. McKane
Assistant Examiner—Kamal Saeed
(74) Attorney, Agent, or Firm—Stephen E. Reiter; Foley & Lardner

(57) ABSTRACT

In accordance with the present invention, there are provided compounds and pharmaceutical compositions useful for the selective inhibition of COX-2 in the presence of COX-1. As a result, invention compounds and compositions provide anti-inflammatory relief to a subject in need thereof while dramatically reducing the occurrence of side effects in the subject. Compounds contemplated for use in the practice of the present invention are substituted heterocyclic compounds containing amidinyl and imidazolyl groups.

24 Claims, 3 Drawing Sheets

HETEROARYL SUBSTITUTED AMIDINYL AND IMIDAZOLYL COMPOUNDS AND METHODS EMPLOYING SAME FOR THE TREATMENT OF INFLAMMATION

FIELD OF THE INVENTION

The present invention relates to pharmaceutical agents. In particular, the present invention relates to compounds, pharmaceutical formulations, and methods useful for treating inflammation and inflammation-related disorders, such as, for example, arthritis.

BACKGROUND OF THE INVENTION

Nonsteroidal anti-inflammatory drugs (NSAIDs) are one of the most frequently used pharmacological agents worldwide. They are commonly prescribed for the relief of pain, stiffness, and joint swelling for patients with osteoarthritis and rheumatoid arthritis, conditions estimated to affect 12.1% and 1.0%, respectively, of adults in the United States (Lawrence R C, Helmick C G, Arnett F C, et al. "Estimates of the prevalence of arthritis and selected musculoskeletal disorders in the United States" Arthritis Rheum (1998) 41 (5): 778–99).

Although NSAIDs are generally well tolerated, upper gastrointestinal adverse events are frequently associated with their use. Symptoms range from dyspepsia, nausea, and abdominal pain to more serious complications of mucosal ulceration such as bleeding and perforation. Such upper gastrointestinal complications are the most frequent serious complication of NSAID use and are probably contributory to most NSAID-related deaths. Approximately 16,500 NSAID-related deaths are estimated to occur annually in the US (among 13 million patients exposed to the drugs, see Singh G., Triadafilopoulos G., "Epidemiology of NSAID induced gastrointestinal complications" J. Rheumatol., (1999) 26 Suppl. 56: 18–24).

NSAIDs act by inhibiting the activity of the enzyme cyclo-oxygenase (COX), and thereby prostaglandin and thromboxane production. COX exists as two isoforms, COX-1 and COX-2. The gastrointestinal adverse events associated with long term NSAID use are believed to result from the inhibition of COX-1. Other less frequent adverse events such as bleeding complications, fluid and electrolyte disorders, acute renal failure, and renal papillary necrosis have also been attributed to inhibition of this enzyme. In contrast, the anti-inflammatory and analgesic effects of NSAIDs are thought to result from inhibition of COX-2.

Certain 1, 2, 4- and 1, 3, 4-thiadiazoles bearing tert-butylphenol moieties and other structurally related compounds are known to provide activity as inhibitors of cyclooxygenase and/or 5-lipoxygenase (see, for example, U.S. Pat. No. 5,510,361 to Scherz; Song Y., Conner D. T., Sercel A. D., Sorenson R. J., Doubleday R., J. Med. Chem. Vol. 42 (1999), pp. 1161–1169; Mullican M. D., Wilson M. W., Connor D. T., Kostlan C. R., Schrier D. J., Dyer R. D., J. Med. Chem., Vol. 36 (1993), pp. 1090–1099). However, there are very few known compounds that are able to selectively inhibit COX-2 in the presence of COX-1 (see U.S. Pat. No. 5,616,601 to Khanna, et al.).

Accordingly, there is a need for compounds and pharmaceutical compositions useful for selectively inhibiting COX-2 in the presence of COX-1, thereby minimizing the pathological side effects associated with NSAID use while maximizing the desired anti-inflammatory and analgesic effects provided by NSAIDs.

SUMMARY OF THE INVENTION

In accordance with the present invention, there are provided compounds and pharmaceutical compositions useful for the selective inhibition of COX-2 in the presence of COX-1. As a result, invention compounds and compositions provide anti-inflammatory relief to a subject in need thereof while dramatically reducing the occurrence of side effects in the subject. Compounds contemplated for use in the practice of the present invention are substituted heterocyclic compounds containing amidinyl and imidazolyl groups.

In accordance with additional embodiments of the present invention, there are provided methods for treating inflammation related conditions, methods for treating pathological conditions of the skin, methods for reducing side effects associated with anti-inflammatory agents, and methods for selectively inhibiting COX-2 in the presence of COX-1.

DETAILED DESCRIPTION OF THE INVENTION

Figure 1:
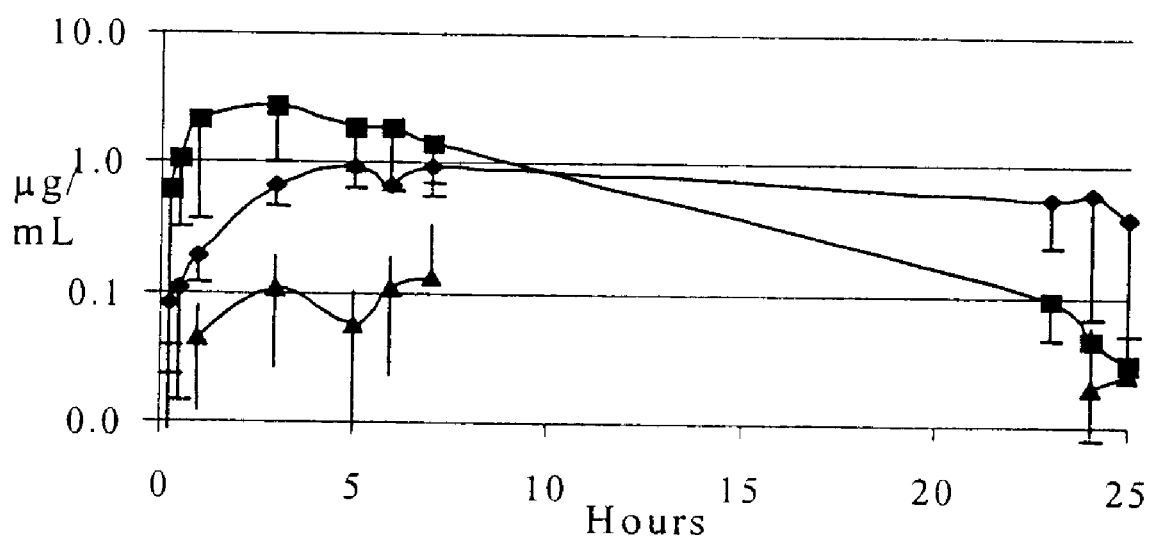
FIG. 1 illustrates pharmacokinetic data for Celecoxib™ (□), invention compound Example 48 (MX-1297) (◇), and invention compound Example 44 (MX-1265) (△) after oral administration in rats.

In accordance with the present invention, there are provided compounds having the following structure:

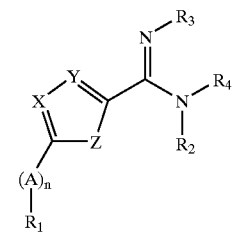

wherein:
X and Y are each independently C or N,
Z is N, O, or S,
$R_1$ and $R_2$ are each independently optionally substituted aryl or heteroaryl,
$R_3$ and $R_4$ are each independently hydrogen or lower alkyl, or $R_3$ and $R_4$ can cooperate to form an optionally substituted ring, wherein said ring includes the amidinyl moiety to which $R_3$ and $R_4$ are attached,
A is $CH_2$, $NR_5$, O, or S, wherein $R_5$ is hydrogen or lower alkyl, and
n is 0 or 1.

As employed herein, "aryl" refers to aromatic groups having from 5 to about 10 carbon atoms, optionally bearing one or more substituents selected from hydroxyl, halogen, cyano, nitro, carboxyl, optionally substituted alkyl, optionally substituted alkenyl, optionally substituted alkynyl, optionally substituted aryl, optionally substituted alkoxy, optionally substituted thioalkyl, amino, amido, alkylamino, arylamino, aminosulfonyl, alkylsulfonyl, alkoxycarbonyl, mercapto, cycloalkyl, optionally substituted heterocyclic, optionally substituted heteroaryl, aryloxy, nitrone, C(O)H, acyl, oxyacyl, carbamate, sulfonamide, sulfuryl, and the like.

As employed herein, "heteroaryl" refers to aromatic groups containing one or more heteroatoms (e.g., N, O, S, or the like) as part of the ring structure, and having in the range of 3 up to 10 carbon atoms, optionally bearing one or more substituents as set forth above.

As employed herein, "alkyl" refers to hydrocarbyl radicals having 1 up to 20 carbon atoms, preferably 2–10 carbon atoms, and "substituted alkyl" refers to alkyl groups further bearing one or more substituents as set forth above.

As employed herein, "lower alkyl" refers to hydrocarbyl radicals having 1 up to 6 carbon atoms, optionally bearing one or more substituents as set forth above.

As employed herein, "alkoxy" refers to the moiety -O-alkyl-, wherein alkyl is as defined above, and "substituted alkoxy" refers to alkoxy groups further bearing one or more substituents as set forth above.

As employed herein, "lower alkoxy" refers to the moiety -O-alkyl-, wherein alkyl refers to hydrocarbyl radicals having 1 up to 6 carbon atoms, and "substituted lower alkoxy" refers to alkoxy groups further bearing one or more substituents as set forth above.

As employed herein, "thioalkyl" refers to the moiety -S-alkyl-, wherein alkyl is as defined above, and "substituted thioalkyl" refers to thioalkyl groups further bearing one or more substituents as set forth above.

As employed herein, "lower thioalkyl" refers to the moiety -S-alkyl-, wherein alkyl refers to hydrocarbyl radicals having 1 up to 6 carbon atoms, and "substituted lower thioalkyl" refers to thioalkyl groups further bearing one or more substituents as set forth above.

As employed herein, "cycloalkyl" refers to cyclic (i.e., ring-containing) groups containing in the range of about 3 up to 8 carbon atoms, and "substituted cycloalkyl" refers to cycloalkyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynylene groups further bearing one or more substituents as set forth above.

In one aspect of the present invention, $R_1$ and $R_2$ are each independently optionally substituted aryl. Preferably, $R_1$ and $R_2$ are each independently optionally substituted phenyl, naphthyl, biphenyl, or the like.

In another aspect of the present invention, $R_1$ and $R_2$ are each independently optionally substituted heteroaryl. Preferably, $R_1$ and $R_2$ are each independently optionally substituted furyl, benzofuryl, benzodioxolyl, imidazolyl, benzimidazolyl, pyrrolyl, thienyl, thiazolyl, oxazolyl, isoxazolyl, triazolyl, indolyl, pyrimidinyl, pyrazolyl, quinolinyl, pyridyl, or the like.

In aspects of the invention wherein $R_1$ and $R_2$ are substituted, the substituents are preferably hydroxyl, halogen, cyano, nitro, carboxyl, optionally substituted alkyl, aryl, alkoxy, thioalkyl, amino, alkylamino, arylamino, aminosulfonyl, alkylsulfonyl, alkoxycarbonyl, or the like. More preferably the substituents are halogen, haloalkyl, alkyl, alkoxycarbonyl, alkylsulfonyl, aminosulfonyl, or the like.

In an alternate aspect of the invention, $R_3$ and $R_4$ are each hydrogen, thereby forming an amidinyl moiety.

In another alternate aspect of the invention, $R_3$ and $R_4$ cooperate to form an optionally substituted 5-, 6-, or 7-membered ring. In a preferred embodiment, $R_3$ and $R_4$ cooperate to form an optionally substituted 5-membered ring. When the 5-membered ring is substituted, preferred substituents are hydroxy, halogen, optionally substituted alkyl, aryl, aralkyl, heteroaryl, heterocyclic, alkoxy, aryloxy, thioalkyl, thioaryl, acyl, cyano, sulfonyl, alkylsulfonyl, alkylcarbonyl, arylcarbonyl, amino, carboxyl, aminocarbonyl, or the like. Presently most preferred substituents are lower alkyl, haloalkyl, halogen, lower alkoxy, lower thioalkyl, heteroaryl, heterocyclic, or the like.

Pharmaceutically acceptable salts of invention compounds are also contemplated for use in the practice of the present invention. Pharmaceutically acceptable salts within the scope of the invention may be those derived from mineral acids such as, for example, hydrochloric acid and sulfuric acid, resulting in the corresponding hydrochloride or sulfonate, respectively. In addition, pharmaceutically acceptable salts may be derived from organic acids such as ethanesulfonic acid, benzenesulfonic acid, p-toluenesulfonic acid, and the like, giving the corresponding ethanesulfonate, benzenesulfonate, p-toluenesulfonate, and the like, respectively.

Invention compounds are readily prepared in a variety of ways, e.g., by converting the cyano functional group on the precursor 5-cyano-1, 3, 4-thiadiazoles (i.e., compounds 5 and 10) into an amidinyl or imidazolyl moiety. Exemplary methods for synthesizing precursor compounds 5 and 10 are illustrated below in Scheme 1.

Scheme 1
General Procedure for the Synthesis of
5-cyano-1,3,4-thiadiazoles

Method A

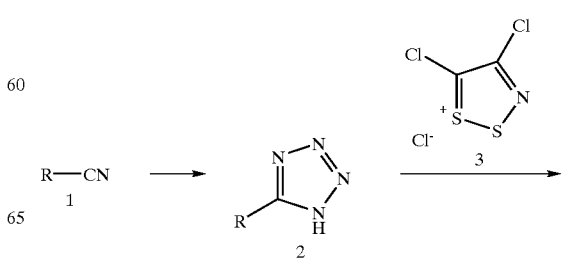

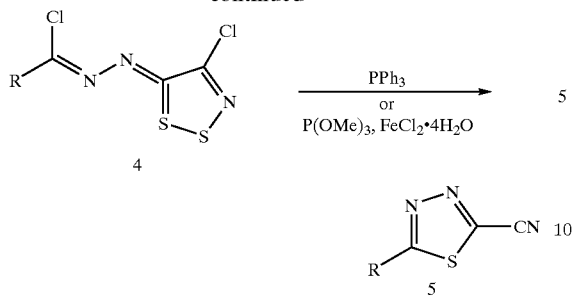

Method B

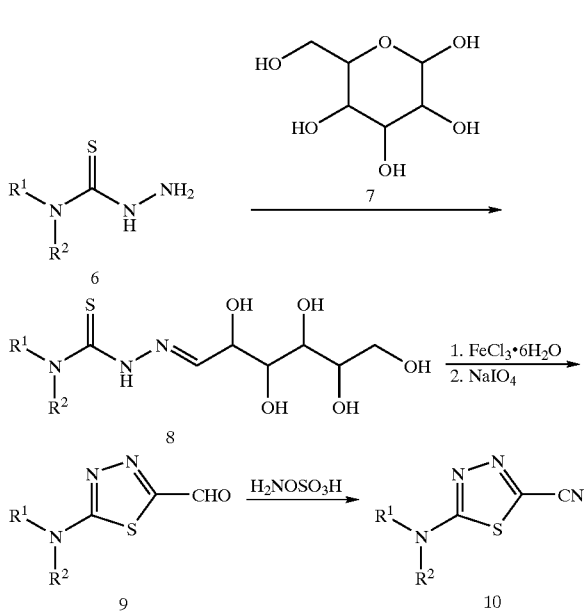

In synthetic method A, a nitrile 1 can be converted to a tetrazole 2 by known procedures (Koguro, Kiyoto; Oga, Toshikazu; Mitsui, Sunao; Orita, Ryozo, Synthesis (1998), (6), 910–914). Tetrazole 2 is then treated with 4,5-dichloro-1,2,3-dithiazolium chloride 3 (Appel Salt, Le, V.-D. et. al. (2001) Tet. Lett., 41, 9407) in chlorinated solvents such as, e.g., dichloromethane, chloroform, dichloroethane, carbon tetrachloride at room temperature for 1 to 24 hrs to afford hydrazonoyl chloride 4. Reaction of hydrazonoyl chloride 4 with thiophilic reagents such as triphenylphosphine, trialkylphosphite/$FeCl_2 \cdot 4H_2O$, or dimethylsulfoxide in chlorinated solvents at room temperature for 1 to 24 hrs affords 2-substituted 1,3,4-thiadiazole-5-carbonitrile 5.

In synthetic method B, precursor compounds of structure 10 are prepared by treating thiosemicarbazide 6 and sugar 7 in a solvent mixture of ethanol and water at refluxing conditions for 1 to 4 hrs to afford 8 (Ashry, E. S. H. et. al. (1987) Bull. Chem.Soc. Jpn., 60, 3405). Compound 9 can be prepared by treating 8 with $FeCl_3 \cdot 6H_2O$ in ethanol followed by oxidation with sodium periodate at room temperature. Treatment of 9 with hydroxylamine-O-sulfonic acid in ethanol in the presence of bases such as trialkylamines and pyridines at refluxing conditions for 12 to 24 hrs gives precursor compound 10.

A general synthetic scheme for the preparation of invention amidinyl compounds 13 is illustrated in Scheme 2.

Scheme 2
General Synthesis of Invention
Amidinyl Compounds

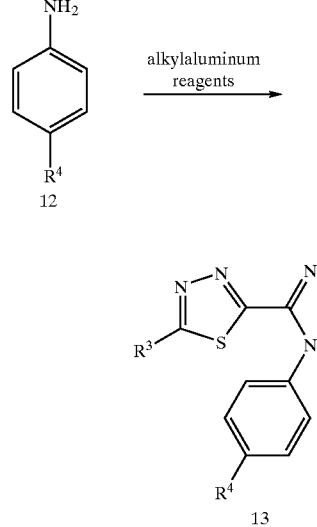

The precursor 5-cyano-1,3,4-thiadiazole 11 is reacted with anilines 12 in the presence of alkylaluminum reagents such as trimethylaluminum, triethylaluminum, dimethylaluminum chloride, diethylaluminum chloride, and the like, to afford invention compounds 13.

A general synthetic scheme for the preparation of invention imidazolyl compounds 15 and 20 is illustrated in Scheme 3.

Scheme 3
General Synthesis of Invention
Imidazolyl Compounds

Method A

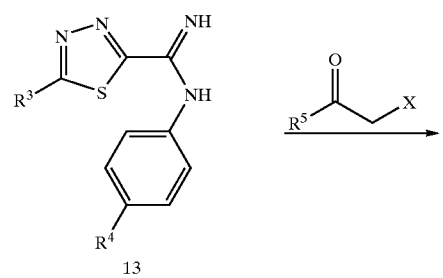

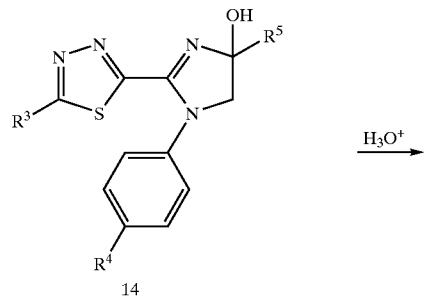

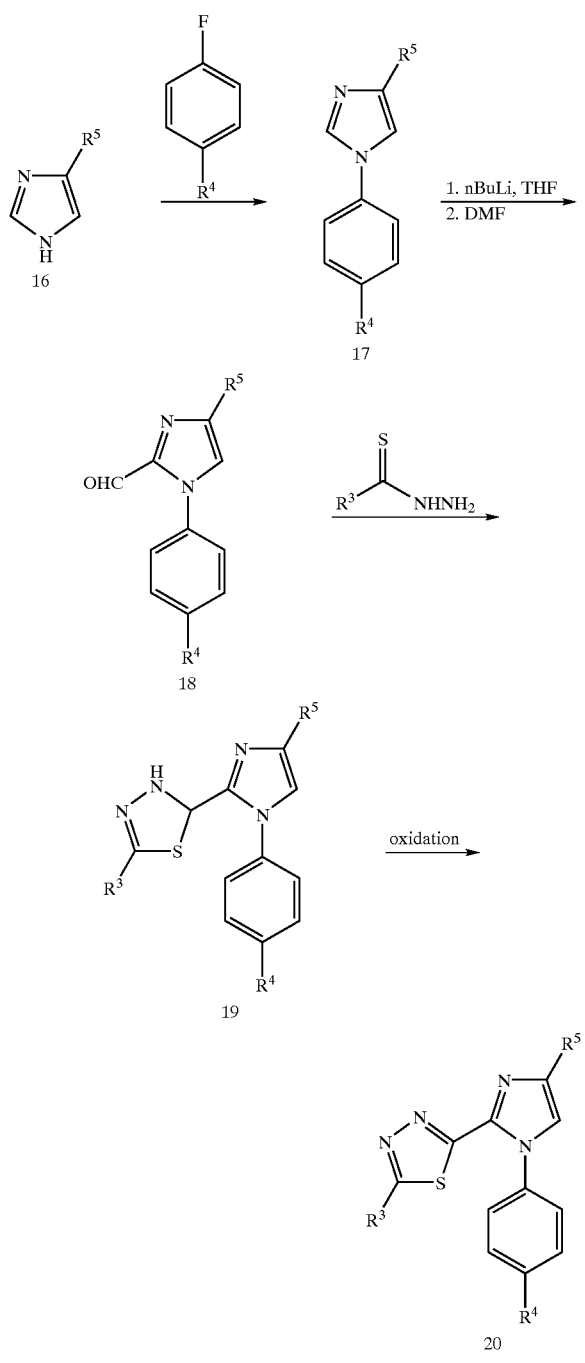

In method A, amidine 13 is reacted with a 2-halo-ketone (X=Br or Cl) in the presence of bases such as sodium bicarbonate, potassium carbonate, sodium carbonate, potassium bicarbonate, N,N'-diisopropylethylamine, or the like, to afford the alkylated product 14. Suitable solvents for this reaction are polar solvents such as, for example, isopropanol, acetone, or dimethylformamide. The reaction may be carried out at 20° C. to 90° C. The intermediate 14 is dehydrated in the presence of an acid catalyst such as p-toluenesulfonic acid to give invention compounds 15. Suitable solvents for this dehydration step are aromatic solvents, e.g., toluene, xylene, benzene (Method A).

Alternatively, method B illustrates an exemplary method for the preparation of invention compounds of structure 20, i.e., by treating 4-substituted imidazole 16 and a 1-fluoro-4-substituted phenyl compound ($R_4=SO_2Me$, $NO_2$) in dimethylformamide at 60° C. to 120° C. 1 to 12 hrs to afford 17. Aldehyde 18 can then be prepared by treating 17 with n-BuLi in a suitable solvent, such as, for example, ether or tetrahydrofuran at −50° C. to −78° C. followed by quenching with a formylating agent such as, for example, dimethylformamide or N-formylmorpholine. Treatment of 18 with thiosemicarbazide or thiohydrazide in ethanol at refluxing conditions for 1 to 4 hrs, followed by oxidation of compound 19 with a suitable oxidizing agent, affords invention compounds 20. Suitable oxidizing agents include $FeCl_3$ and DDQ.

Invention compounds are useful for a variety of therapeutic applications, e.g., for the treatment of inflammation and inflammation-related disorders in a subject, while markedly reducing the occurrence of side effects in the subject. For example, invention compounds may be used as an analgesic in the treatment of pain and headaches, especially migraine headaches, or as an antipyretic for the treatment of fever. Invention compounds are particularly useful in the treatment of conditions such as, for example, arthritis, rheumatoid arthritis, spondyloarthopathies, gouty arthritis, osteoarthritis, systemic lupus erythematosus, juvenile arthritis, gastrointestinal conditions (e.g., inflammatory bowel disease, Crohn's disease, gastritis, irritable bowel syndrome, ulcerative colitis, and the like), for the prevention of colorectal cancer, and the like.

Invention compounds are also useful in the treatment of asthma, bronchitis, menstrual cramps, tendinitis, bursitis, skin related conditions (such as, for example, psoriasis, eczema, burns, dermatitis, and the like), and the like. In addition, invention compounds are useful in treating inflammation occurring in diseases such as, for example, vascular diseases, periarteritis nodosa, thyroidiris, aplastic anemia, Hodgkin's disease, sclerodoma, rheumatic fever, type I diabetes, myasthenia gravis, sarcoidosis, nephrotic syndrome, Behcet's syndrome, potymyositis, gingivitis, hypersensitivity, conjunctivitis, swelling occurring after injury, myocardial ischemia, and the like.

Besides being useful for human treatment, invention compounds and formulations containing same are also useful for treatment of other mammals, including horses, cows, dogs, cats, rats, mice, sheep, pigs, and the like.

While not wishing to be bound by theory, it is believed that the observed therapeutic benefits provided by invention compounds result from the ability of invention compounds to selectively inhibit cyclooxygenase-2 in the presence of cyclooxygenase-1. Illustrating this aspect, invention compounds have been found to be more than 10–90 times more effective in inhibiting COX-2 than they are at inhibiting COX-1. In addition, all invention compounds have a COX-2 $IC_{50}$ of 1 nM to 1 μM. By way of comparison, Celecoxib™ has an $IC_{50}$ for COX-2 of 3.4 nM, and Indomethacin has an $IC_{50}$ for COX-2 of approximately 6.1 $\mu$M.

Thus, in accordance with this aspect of the invention, there are provided methods for reducing side effects associated with administration of anti-inflammatory agents to a subject in need thereof and methods for selectively inhibiting COX-2 in the presence of COX-1, comprising administering to the subject invention heteroaryl substituted amidinyl or imidazolyl compounds.

The ability of invention compounds to treat cyclooxygenase (COX) mediated diseases can be demonstrated by measuring the amount of prostaglandin $E_2$ ($PGE_2$) synthesized in the presence of arachidonic acid, cyclooxygenase-1 (COX-1) or cyclooxygenase-2 (COX-2), and an invention compound. The $IC_{50}$ values represent the concentration of inhibitor required to return $PGE_2$ synthesis to 50% of that obtained as compared to the uninhibited control.

Depending on the mode of delivery employed, the compounds contemplated for use herein can be delivered in a variety of pharmaceutically acceptable forms. For example, invention compounds can be delivered in the form of a solid, solution, emulsion, dispersion, micelle, liposome, and the like.

Thus, in accordance with still another embodiment of the present invention, there are provided pharmaceutical formulations comprising invention compounds in a suitable vehicle rendering said compounds amenable to oral delivery, transdermal delivery, intravenous delivery, intramuscular delivery, topical delivery, nasal delivery, and the like.

Pharmaceutical compositions of the present invention can be used in the form of a solid, a solution, an emulsion, a dispersion, a micelle, a liposome, and the like, wherein the resulting composition contains one or more of the compounds of the present invention as an active ingredient, in admixture with an organic or inorganic carrier or excipient suitable for enteral or parenteral applications. Invention compounds may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable-dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compounds contemplated for use in the practice of the present invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner. In general, the dosage of invention compounds employed as described herein falls in the range of about 0.01 mmoles/kg body weight of the subject/hour up to about 0.5 mmoles/kg/hr. Typical daily doses, in general, lie within the range of from about 10 $\mu$g up to about 100 mg per kg body weight, and, preferably within the range of from 50 $\mu$g to 10 mg per kg body weight and can be administered up to four times daily. The daily IV dose lies within the range of from about 1 $\mu$g to about 100 mg per kg body weight, and, preferably, within the range of from 10 $\mu$g to 10 mg per kg body weight.

The invention will now be described in greater detail by reference to the following non-limiting examples.

Examples 1–52 illustrate the preparation of specific compounds of the present invention as well as intermediates useful in preparing compounds of the present invention. All reagents were used as received without purification. $^1$H and $^{13}$C NMR spectra were obtained on a Varian VXR-500 nuclear magnetic resonance spectrometer.

EXAMPLE 1

3-Chloro-1-(4-chloro-5H-1,2,3-dithiazol-5-ylideno)-3-(2-hydroxyphenyl)-1,2-diazoprop-2-ene A mixture of 5-(2-hydroxyphenyl)-tetrazole (1.74 g, 10.7 mmol) and 4,5-dichloro-1,2,3-dithiazolium chloride (2.46 g, 11.8 mmol) in dichloromethane (100 mL) was stirred at room temperature for 4 hours. The crude product was purified by flash chromatography using hexane/$CH_2Cl_2$ as an eluent to give the product (2.9 g, 89%) as a yellow solid; $^1$H NMR δ (DMSO-$d_6$) 10.7 (1H, bs), 7.81 (1H, d, J=7.7 Hz), 7.47 (1H, t, J=7.7 Hz), 7.02 (2H, m) $^{13}$C NMR δ (DMSO-$d_6$) 165.7, 157.3, 149.7, 142.6, 133.9, 130.5, 119.7, 117.7, 117.1.

EXAMPLE 2

2-(2-Hydroxyphenyl)-1,3,4-thiadiazole-5-carbonitrile

A mixture of 3-chloro-1-(4-chloro-5H-1,2,3-dithiazol-5-ylideno)-3-(2-hydroxyphenyl)-1,2-diazoprop-2-ene (0.83 g, 2.86 mmol) and triphenylphosphine (1.58 g, 6.01 mmol) in dichloromethane (40 mL) was stirred at room temperature for 1 hour and evaporated in vacuo to dryness. The crude product was purified by flash chromatography on silica gel using hexane/ethyl acetate as an eluent to give the product (0.39 g, 67%) as a white solid; $^1$H NMR δ (DMSO-$d_6$) 10.8 (1H, bs), 7.54 (1H, d, J=8.2 Hz), 7.50 (1H, t, J=8.1 Hz), 7.15 (1H, d, J=8.4 Hz), 7.03 (1H, t, J=7.6 Hz); $^{13}$C NMR δ (DMSO-$d_6$) 173.0, 158.0, 137.1, 135.3, 130.2, 121.0, 119.1, 110.1, 29.9.

EXAMPLE 3

3-Chloro-1-(4-chloro-5H-1,2,3-dithiazol-5-ylideno)-3-(4-methylthiophenyl)-1,2-diazoprop-2-ene A mixture of 5-(4-methylthiophenyl)-tetrazole (5.83 g, 30.4 mmol) and 4,5-dichloro-1,2,3-dithiazolium chloride (6.96 g, 33.4 mmol) in dichloromethane (140 mL) was stirred at room temperature for 4 hours. The crude product was purified by flash chromatography using hexane/$CH_2Cl_2$ as an eluent to give the product (8.24 g, 81%) as a yellow solid; $^1$H NMR δ (DMSO-$d_6$) 7.95 (2H, d, J=8.7 Hz), 7.40 (2H, d, J=8.6 Hz), 2.55 (3H, s); $^{13}$C NMR δ (DMSO-$d_6$) 166.3, 147.8, 145.1, 142.7, 128.7, 128.6, 125.3, 14.0.

EXAMPLE 4

2-(4-Methylthiophenyl)-1,3,4-thiadiazole-5-carbonitrile

A mixture of 3-chloro-1-(4-chloro-5H-1,2,3-dithiazol-5-ylideno)-3-(4-methylthiophenyl)-1,2-diazoprop-2-ene (0.5 g, 1.49 mmol) and triphenylphosphine (0.82 g, 3.13 mmol) in dichloromethane (40 mL) was stirred at room temperature for 1 hour and evaporated in vacuo to dryness. The crude product was purified by flash chromatography on silica gel using hexane/ethyl acetate as an eluent to give the product (0.29 g, 84%) as a white solid; $^1$H NMR δ (DMSO-$d_6$) 7.98 (2H, d, J=8.1 Hz), 7.43 (2H, d, J=8.7 Hz), 2.56 (3H, s); $^{13}$C NMR δ (DMSO-$d_6$) 172.2, 145.2, 138.8, 128.7, 125.9, 123.9, 111.1, 14.0.

EXAMPLE 5

2-(4-Fluorophenyl)-1,3,4-thiadiazole-5-carbonitrile

To a stirred solution of 3-chloro-1-(4-chloro-5H-1,2,3-dithiazol-5-ylideno)-3-(4-fluorophenyl)-1,2-diazoprop-2-ene (1.29 g, 4.19 mmol) and trimethylphosphite (2.08 g, 16.8 mmol) in $CH_2Cl_2$/THF (80 mL, 1:1) was added $FeCl_2.4H_2O$ (1.67 g, 8.38 mmol). The reaction mixture was stirred overnight at room temperature, then excess solvent was removed. The residue was redissolved in ethyl acetate and washed with water and brine. The organic fraction was dried ($Na_2SO_4$) and evaporated to dryness. The residue was purified by flash chromatography on silica gel using hexane/ethyl acetate as an eluent to give the product (0.69 g, 80%) as a white solid; $^1$H NMR δ (DMSO-$d_6$) 8.15 (1H, d, J=8.2 Hz), 8.14 (1H, d, J=8.4 Hz), 7.45 (2H, t, J=8.7 Hz); $^{13}$C NMR δ (DMSO-$d_6$) 171.4, 165.6, 163.6, 139.6, 131.1, 131.0, 124.6, 117.0, 116.8, 110.9.

EXAMPLE 6

2-(6-Methoxy-2-naphthyl)-1,3,4-thiadiazole-5-carbonitrile

Following the procedure of Example 5, 3-chloro-1-(4-chloro-5H-1,2,3-dithiazol-5-ylideno)-3-(6-methoxy-2-naphthyl)-1,2-diazoprop-2-ene (2.16 g, 5.84 mmol) was reacted with trimethylphosphite (2.90 g, 23.4 mmol) and $FeCl_2.4H_2O$ (2.32 g, 11.7 mmol) in $CH_2Cl_2$/THF (100 mL, 1:1) to give the product (1.38 g, 88%) as a white solid; $^1$H NMR δ (DMSO-$d_6$) 8.61 (1H, s), 8.06 (1H, d, J=8.9 Hz), 8.02 (1H, d, J=8.9 Hz), 7.97 (1H, d, J=8.5 Hz), 7.42 (1H, d, J=2.2 Hz), 7.27 (1H, dd, J=8.9, 2.2 Hz), 3.92 (3H, s); $^{13}$C NMR δ (DMSO-$d_6$) 163.9, 150.3 129.8, 127.5, 121.7, 120.2, 119.1, 118.9, 115.7, 113.9, 111.1, 102.1, 97.3, 46.4.

EXAMPLE 7

2-(3-Hydroxyphenyl)-1,3,4-thiadiazole-5-carbonitrile

Following the procedure of Example 5, 3-chloro-1-(4-chloro-5H-1,2,3-dithiazol-5-ylideno)-3-(3-hydroxyphenyl)-1,2-diazoprop-2-ene (0.8 g, 2.61 mmol) was reacted with trimethylphosphite (1.30 g, 10.5 mmol) and $FeCl_2.4H_2O$ (1.04 g, 5.23 mmol) in $CH_2Cl_2$/THF (50 mL, 1:1) to give the product (0.3 g, 56%) as white a solid; $^1$H NMR δ (DMSO-$d_6$) 10.1 (1H, s), 7.46 (1H, d, J=8.3 Hz), 7.45 (1H, s), 7.39 (1H, t, J=7.9 Hz), 7.04 (1H, d, J=7.7 Hz); $^{13}$C NMR δ DMSO-$d_6$) 172.6, 158.2, 139.3, 131.0, 128.9, 120.0, 119.4, 114.4, 111.0.

EXAMPLE 8

2-(3, 4-Methylenedioxyphenyl)-1,3,4-thiadiazole-5-carbonitrile

Following the procedure of Example 2, 3-chloro-1-(4-chloro-5H-1,2,3-dithiazol-5-ylideno)-3-(3,4-methylenedioxyphenyl)-1,2-diazoprop-2-ene (1.13 g, 3.38 mmol) was reacted with triphenylphosphine (2.13 g, 8.12 mmol) in dichloromethane (80 mL) to give the product (0.56 g, 72%) as a white solid; $^1$H NMR δ (DMSO-$d_6$) 7.63 (2H, m), 7.12 (1H, d, J=8.0 Hz), 6.18 (2H, s); $^{13}$C NMR δ (DMSO-$d_6$) 172.2, 151.2, 148.4, 138.6, 124.3, 121.7, 111.1, 109.3, 107.7, 102.4.

EXAMPLE 9

2-(3,4,5-Trimethoxyphenyl)-1,3,4-thiadiazole-5-carbonitrile

Following the procedure of Example 5, 3-chloro-1-(4-chloro-5H-1,2,3-dithiazol-5-ylideno)-3-(3,4,5-trimethoxyphenyl)-1,2-diazoprop-2-ene (2.08 g, 5.47 mmol)

was reacted with trimethylphosphite (2.72 g, 21.9 mmol) and $FeCl_2.4H_2O$ (2.18 g, 10.9 mmol) in $CH_2Cl_2$/THF (80 mL, 1:1) to give the product (1.2 g, 79%) as a white solid; $^1H$ NMR δ (DMSO-$d_6$) 7.33 (2H, s), 3.89 (6H, s), 3.76 (3H, s); $^{13}C$ NMR δ (DMSO-$d_6$) 172.3, 153.5, 141.3, 139.2, 123.1, 111.1, 106.0, 60.3, 56.3.

EXAMPLE 10

2-(3,5-Di-tert-butyl-4-hydroxyphenyl)-1,3,4-thiadiazole-5-carbonitrile

Following the procedure of Example 5, 3-chloro-1-(4-chloro-5H-1,2,3-dithiazol-5-ylideno)-3-(3,5-di-tert-butyl-4-hydroxyphenyl)-1,2-diazoprop-2-ene (1.73 g, 4.14 mmol) was reacted with trimethylphosphite (2.05 g, 16.6 mmol) and $FeCl_2.4H_2O$ (1.65 g, 8.28 mmol) in $CH_2Cl_2$/THF (80 mL, 1:1) to give the product (1.09 g, 83%) as a white solid; $^1H$ NMR δ (DMSO-$d_6$) 7.99 (1H, s), 7.74 (2H, s), 1.42 (18H, s); $^{13}C$ NMR δ (DMSO-$d_6$) 173.3, 158.4, 137.7, 125.3, 119.3, 111.0, 34.5, 29.8.

EXAMPLE 11

2-(3,4,5-Trimethoxybenzylidinyl)-1,3,4-thiadiazole-5-carbonitrile

Following the procedure of Example 2, 3-chloro-1-(4-chloro-5H-1,2,3-dithiazol-5-ylideno)-3-(3,4,5-trimethoxybenzylidinyl)-1,2-diazoprop-2-ene (0.44 g, 1.12 mmol) was reacted with triphenylphosphine (0.70 g, 2.68 mmol) in dichloromethane (40 mL) to give the product (0.21 g, 65%) as a white solid; $^1H$ NMR δ (DMSO-$d_6$) 6.73 (2H, s), 4.54 (2H, s), 3.75 (6H, s), 3.64 (3H, s); $^{13}C$ NMR δ (DMSO-$d_6$) 175.8, 153.2, 140.4, 136.8, 132.3, 111.1, 106.4, 60.0, 55.9, 35.1.

EXAMPLE 12

2-(3-Methoxy-4-hydroxyphenyl)-1,3,4-thiadiazole-5-carbonitrile

Following the procedure of Example 5, 3-chloro-1-(4-chloro-5H-1,2,3-dithiazol-5-ylideno)-3-(3-methoxy-4-hydroxyphenyl)-1,2-diazoprop-2-ene (1.68 g, 5.0 mmol) was reacted with trimethylphosphite (2.48 g, 20.0 mmol) and $FeCl_2.4H_2O$ (1.99 g, 10.0 mmol) in $CH_2Cl_2$/THF (100 mL, 1:1) give the product (0.89 g, 76%) as a white solid; $^1H$ NMR δ (DMSO-$d_6$) 10.2 (1H, s), 7.57 (1H, d, J=1.6Hz), 7.51 (1H, dd, J=8.6, 1.6Hz), 6.94 (1H, d, J=8.4Hz), 3.88(3H, s); $^{13}C$ NMR δ (DMSO-$d_6$) 172.7, 151.4, 148.3, 137.9, 123.0, 119.0, 116.3, 111.3, 111.2, 55.8.

EXAMPLE 13

2-(3-Benzyloxyphenyl)-1,3,4-thiadiazole-5-carbonitrile

Following the procedure of Example 5, 3-chloro-1-(4-chloro-5H-1,2,3-dithiazol-5-ylideno)-3-(3-benzyloxyphenyl)-1,2-diazoprop-2-ene (0.78 g, 1.97 mmol) was reacted with trimethylphosphite (0.98 g, 7.88 mmol) and $FeCl_2.4H_2O$ (0.78 g, 3.94 mmol) in $CH_2Cl_2$/THF (100 mL, 1:1) to give the product (0.39 g, 67%) as a white solid; $^1H$ NMR δ (DMSO-$d_6$) 7.89 (1H, s), 7.64 (1H, d, J=7.6 Hz), 7.52 (1H, t, J=8.1 Hz), 7.49 (2H, d, J=7.6 Hz), 7.41 (2H, d, J=7.4 Hz), 7.35 (1H, d, J=7.2 Hz), 7.32 (1H, dd, J=8.5, 2.2 Hz), 5.22 (2H, s); $^{13}C$ NMR δ (DMSO-$d_6$) 172.3, 158.9, 139.6, 136.5, 131.0, 129.1, 128.5, 128.0, 127.8, 121.1, 119.5, 114.0, 111.0, 69.6.

EXAMPLE 14

2-Methylthio-1,3,4-thiadiazole-5-carbonitrile

Following the procedure of Example 5, 3-chloro-1-(4-chloro-5H-1,2,3-dithiazol-5-ylideno)-3-(methylthio)-1,2-diazoprop-2-ene (12.1 g, 53.1 mmol) was reacted with trimethylphosphite (26.3 g, 212 mmol) and $FeCl_2.4H_2O$ (21.1 g, 106 mmol) in $CH_2Cl_2$/THF (400 mL, 1:1) to give the product (6.7 g, 80%) as a white solid; $^1H$ NMR δ (DMSO-$d_6$) 2.85 (3H, s); $^{13}C$ NMR δ (DMSO-$d_6$) 174.8, 138.9, 110.8, 16.8.

EXAMPLE 15

2-Methyl-1,3,4-thiadiazole-5-carbonitrile

Following the procedure of Example 5, 3-chloro-1-(4-chloro-5H-1,2,3-dithiazol-5-ylideno)-3-(methyl)-1,2-diazoprop-2-ene (2.28 g, 10 mmol) was reacted with trimethylphosphite (4.96 g, 40 mmol) and $FeCl_2.4H_2O$ (3.98 g, 20 mmol) in $CH_2Cl_2$/THF (400 mL, 1:1) to give the product (0.91 g, 73%) as a white solid; $^1H$ NMR δ (DMSO-$d_6$) 2.87 (3H, s); $^{13}C$ NMR δ (DMSO-$d_6$) 171.2, 140.1, 111.1, 15.2.

EXAMPLE 16

2-(3,5-Diphenyl-4-hydroxyphenyl)-1,3,4-thiadiazole-5-carbonitrile

Following the procedure of Example 5, 3-chloro-1-(4-chloro-5H-1,2,3-dithiazol-5-ylideno)-3-(3,5-diphenyl-4-hydroxyphenyl)-1,2-diazoprop-2-ene (0.34 g, 0.73 mmol) was reacted with trimethylphosphite (0.36 g, 2.93 mmol) and $FeCl_2.4H_2O$ (0.29 g, 1.46 mmol) in $CH_2Cl_2$/THF (40 mL, 1:1) to give the product (0.12 g, 46%) as a white solid; $^1H$ NMR δ (DMSO-$d_6$) 9.43 (1H, s), 7.89 (2H, s), 7.61 (5H, d, J7.7 Hz), 7.50 (5H, t, J=7.5 Hz), 7.3Hz); $^{13}C$ NMR δ (DMSO-$d_6$) 172.3, 155.0, 138.4, 137.2, 131.8, 130.0, 129.4, 128.4, 127.6, 120.2, 111.2.

EXAMPLE 17

2-Isopropyl-1,3,4-thiadiazole-5-carbonitrile

Following the procedure of Example 5, 3-chloro-1-(4-chloro-5H-1,2,3-dithiazol-5-ylideno)-3-(isopropyl)-1,2-diazoprop-2-ene (1.28 g, 5.0 mmol) was reacted with trimethylphosphite (0.36 g, 20.0 mmol) and $FeCl_2.4H_2O$ (1.99 g, 10 mmol) in $CH_2Cl_2$/THF (40 mL, 1:1) to give the product (0.56 g, 73%) as a white solid; $^1H$ NMR δ ($CDCl_3$) 3.55 (1H, m), 1.47 (6H, d, J=7.2 Hz); $^{13}C$ NMR δ ($CDCl_3$) 181.6, 39.0, 110.4, 31.2, 23.3.

EXAMPLE 18

2-(3, 5-Dimethoxyphenyl)-1,3,4-thiadiazole-5-carbonitrile

Following the procedure of Example 5, 3-chloro-1-(4-chloro-5H-1,2,3-dithiazol-5-ylideno)-3-(3,5-dimethoxyphenyl)-1,2-diazoprop-2-ene (1.31 g, 3.74 mmol) was reacted with trimethylphosphite (1.86 g, 15.0 mmol) and $FeCl_2.4H_2O$ (1.49 g, 7.49 mmol) in $CH_2Cl_2$/THF (40 mL, 1:1) to give the product (0.73 g, 79%) as a white solid; $^1H$ NMR δ (DMSO-$d_6$) 7.15 (2H, d, J=1.9 Hz), 6.77 (1H, d, J=1.9 Hz), 3.83 (6H, s); $^{13}C$ NMR δ (DMSO-$d_6$) 172.3, 161.1, 139.6, 129.5, 111.0, 106.2, 104.5, 55.7, 55.6.

EXAMPLE 19

2-(1-N-Anilino)-1,3,4-thiadiazole-5-carboxyaldehyde

A solution of thiosemicarbazide (2.93 g, 17.5 mmol) and D-galactose (3.79 g, 21.0 mmol) in ethanol (100 mL) and water (10 mL) was heated to reflux for 2 hours. A solution of FeCl$_3$.6H$_2$O (14.2 g, 52.6 mmol) in ethanol (20 mL) was added to the reaction mixture and heated to reflux for 1 hour. The reaction mixture was allowed to cool to room temperature and the precipitate was collected and dried. A suspension of this solid in water (100 mL) was added to a solution of NaIO$_4$ (18.7 g, 87.6 mmol) in water (20 mL). The reaction mixture was stirred at room temperature for 2 hours and the solid was collected and dried to give the product (2.9 g, 81%) as a pale yellow solid; $^1$H NMR δ (DMSO-d$_6$) 11.2 (1H, s), 9.99 (1H, s) 7.66 (2H, s), (2H, s), 7.12 (1H, s); $^{13}$C NMR δ (DMSO-d$_6$) 184.3, 168.0, 158.1, 139.5, 129.3, 123.6, 118.5; MS (m/z): 204.2, (M+, 100%).

EXAMPLE 20

2-(1-N-Anilino)-1,3,4-thiadiazole-5-carbonitrile

To a mixture of 2-(1-N-anilino)-1,3,4-thiadiazole-5-carboxyaldehyde (0.128 g, 0.625 mmol) and hydroxylamine-O-sulfonic acid (0.106 g, 0.938 mmol) in anhydrous ethanol (10 mL), pyridine (1 mL) was added. After heating the reaction mixture at reflux for 2 hours, the solvent was removed. The residue was redissolved in ethyl acetate and washed with 1N HCl, water and brine. The organic fractions were combined, dried over sodium sulfate, filtered and concentrated in vacuo. The crude product was chromatographed (silica gel, hexane/ethyl acetate, 7/3) to give the product (0.120 g, 95%) as a pale yellow solid; 1H NMR δ (DMSO-d$_6$) 11.14 (1H, s), 7.62 (2H, d, J=8.2 Hz), 7.41 (2H, t, J=7.5 Hz), 7.11 (1H, t, J=7.2 Hz); $^{13}$C NMR δ (DMSO-d$_6$) 168.1, 139.3, 129.4, 128.3, 123.6, 118.4, 111.8.

EXAMPLE 21

N-[4-(Methylthio)phenyl]-3-[2-(3,4,5-trimethoxyphenyl)-1,3,4-thiadiazol-5-yl]carboximidamide To a solution of 4-(methylthio)aniline (50 mg, 0.36 mmol) in toluene (4 mL), trimethylaluminum (2M solution in toluene, 0.18 mL, 0.36 mmol) was added over 15 minutes at 0° C. The reaction mixture was warmed to room temperature and stirred for 1 hour. A solution of 2-(3,4,5-trimethoxyphenyl)-1,3,4-thiadiazole-5-carbonitrile (100 mg, 0.36 mmol) in toluene (2 mL) was added over 10 minutes and the reaction mixture was heated to 80–85° C. After 6 hours, the reaction mixture was cooled to room temperature and poured over a slurry of silica gel in chloroform. After filtration, the residue was washed with a mixture of methylene chloride/methanol (2/1). The combined filtrates were concentrated in vacuo and the residue was titurated with a mixture of hexane/ether (2/1). The resulting solid was collected and dried in vacuo, yield=0.13 g (86%); $^1$H NMR δ (DMSO-d$_6$) 7.31 (2H, s), 7.26 (2H, d, J=8.4 Hz), 6.94 (4H, m), 3.89 (6H, s), 3.75 (3H, s), 2.46 (3H, s); $^{13}$C NMR δ (DMSO-d$_6$) 170.4, 167.5, 153.4, 146.9, 145.5, 140.3, 131.6, 127.7, 124.7, 122.4, 105.2, 60.2, 56.2, 15.6.

EXAMPLE 22

N-Hydroxy-3-[(3, 5-di-tert-butyl-4-hydroxyphenyl)-1,3,4-thiadiazol-5-yl]carboximidamide To a solution of 2-(3,5-di-tert-butyl-4-hydroxyphenyl)-1,3,4-thiadiazole-5-carbonitrile (88 mg, 0.28 mmol) and hydroxylamine hydrochloride (40 mg, 0.56 mmol) in DMF (4 mL) was added triethylamine (0.11 g, 1.12 mmol). The reaction mixture was stirred at room temperature for 4 hours and diluted with ethyl acetate (50 mL). The reaction mixture was washed with IN HCl, water and dried and evaporated to dryness. The crude product was purified by chromatography using hexane/ethyl acetate as an eluent to give the product (76 mg, 78%) as a white solid; $^1$H NMR δ (DMSO-d$_6$) 10.4 (1H, s), 7.72 (1H, s), 7.69 (2H, s), 6.17 (2H, s), 3.35 (1H, s), 1.42 (18H, s); $^{13}$C NMR δ (DMSO-d$_6$) 168.8, 160.9, 157.2, 145.5, 139.7, 124.5, 120.8, 34.6, 30.0.

EXAMPLE 23

N-Hydroxy-3-[(3,4,5-trimethoxyphenyl)-1,3,4-thiadiazol-5-yl]carboximidamide

To a solution of 2-(3,4,5-trimethoxyphenyl)-1,3,4-thiadiazole-5-carbonitrile (0.14 g, 0.51 mmol) and hydroxylamine hydrochloride (70 mg, 1.01 mmol) in DMF (4 mL) was added Hunigs' base (0.26 g, 2.02 mmol). The reaction mixture was stirred at room temperature for 4 hours and diluted with ethyl acetate (50 mL). The reaction mixture was washed with 1N HCl, water and dried and evaporated to dryness. The crude product was purified by chromatography using hexane/ethyl acetate as an eluent to give the product (0.11 g, 70%) as a white solid; $^1$H NMR δ (DMSO-d$_6$) 10.5 (1H, s), 7.25 (2H, s), 6.20 (2H, s), 3.88 (6H, s), 3.74 (3H, s); $^{13}$C NMR δ (DMSO-d$_6$) 168.0, 162.1, 153.4, 145.5, 140.3, 124.7, 118.1, 105.3, 60.2, 56.2.

EXAMPLE 24

N-[4-(Methylthio)phenyl]-3-[2-(methylthio)-1,3,4-thiadiazol-5-yl]carboximidamide To a solution of 4-(methylthio)aniline (1.23 g, 8.84 mmol) in toluene (10 mL), trimethylaluminum (2M solution in toluene, 4.42 mL, 8.84 mmol) was added over 15 minutes at 0° C. The reaction mixture was warmed to room temperature and stirred for 1 hour. A solution of 2-(methylthio)-1,3,4-thiadiazole-5-carbonitrile (1.39 g, 8.84 mmol) in toluene (10 mL) was added over 10 minutes and the reaction mixture was heated to 80–85° C. After 6 hours, the reaction mixture was cooled to room temperature and poured over a slurry of silica gel in chloroform. After filtration, the residue was washed with a mixture of methylene chloride/methanol (2/1). The combined filtrates were concentrated in vacuo and the residue was titurated with a mixture of hexane/ether (2/1). The resulting solid was collected and dried in vacuo, yield—2.1 g, 80%; $^1$H NMR δ (DMSO-d$_6$) 7.24 (2H, d, J=8.6 Hz), 6.90 (2H, d, J=8.3 Hz), 2.80 (3H, s), 2.46 (3H, s); $^{13}$C NMR δ (DMSO-d$_6$) 171.1, 167.1, 146.7, 145.4, 131.5, 127.6, 122.4, 16.6, 15.6.

EXAMPLE 25

N-[4-(Methylthio)phenyl]-3-[2-(isopropyl)-1,3,4-thiadiazol-5-yl]carboximidamide

Following the procedure of Example 24, 2-isopropyl-1,3,4-thiadiazole-5-carbonitrile (1.53 g, 10 mmol) was added to a mixture of 4-(methylthio)aniline (1.39 g, 10 mmol) and trimethylaluminum (2M solution in toluene, 5.0 mL, 10 mmol) in toluene (30 mL). The title compound was isolated (1.4 g, 48%) as a brown solid; $^1$H NMR δ (DMSO-d$_6$) 7.24 (2H, d, J=8.1 Hz), 6.90 (2H, d, J=8.5 Hz), 6.84 (2H, bs), 3.45 (1H, m), 2.46 (3H, s), 1.38 (6H, d, J=6.9 Hz); $^{13}$C NMR δ (DMSO-d$_6$) 179.7, 167.0, 147.0, 145.6, 131.4, 127.7, 122.4, 30.2, 23.0, 22.9, 15.6.

EXAMPLE 26

N-Hydroxy-3-[(3, 5-dimethoxyphenyl)-1,3,4-thiadiazol-5-yl]carboximidamide

Following the procedure of Example 23, 2-(3,5-dimethoxyphenyl)-1,3,4-thiadiazole-5-carbonitrile (0.114 g, 0.46 mmol) was reacted with hydroxylamine hydrochloride (64 mg, 0.92 mmol) in the presence of Hunig's base (60 mg, 0.46 mmol) in DMF (2 mL). The crude product was purified by chromatography using hexane/ethyl acetate as an eluent to give the product (0.1 g, 77%) as a white solid; $^1$H NMR δ (DMSO-$d_6$) 10.5 (1H, s), 7.10 (2H, s), 6.9 (1H, s), 6.24 (1H, s), 3.83 (6H, s); $^{13}$C NMR δ (DMSO-$d_6$) 167.9, 162.4, 161.0, 145.4, 130.9, 105.7, 103.3, 55.6, 55.5.

EXAMPLE 27

N-Hydroxy-3-[(3,5-diphenyl-4-hydroxyphenyl)-1,3,4-thiadiazol-5-yl]carboximidamide Following the procedure of Example 26, 2-(3,5-diphenyl-4-hydroxyphenyl)-1,3,4-thiadiazole-5-carbonitrile (0.108 g, 0.30 mmol) was reacted with hydroxylamine hydrochloride (42 mg, 0.61 mmol) in the presence of Hunig's base (79 mg, 0.61 mmol) in DMF (8 mL). The crude product was purified by chromatography using hexane/ethyl acetate as an eluent to give the product (0.1 g, 85%) as a white solid; $^1$H NMR δ (DMSO-$d_6$) 10.5 (1H, s), 9.15 (1H, bs), 7.81 (2H, s), 7.61 (5H, d, J=7.5 Hz), 7.49 (5H, t, J=7.7 Hz), 7.40 (2H, t, J=7.4 Hz), 6.23 (2H, s); $^{13}$C NMR δ (DMSO-$d_6$) 167.7, 161.4, 153.8, 145.5, 137.6, 131.7, 129.4, 129.3, 128.4, 127.5, 121.7.

EXAMPLE 28

N-[4{(2,5-Dimethyl-1H-pyrrol-1-yl)sulfonyl}phenyl]-3-[2-(isopropyl)-1,3,4-thiadiazol-5-yl]carboximidamide To a solution of 1-[(4-aminophenyl)sulfonyl]-2,5-dimethyl-1H-pyrrol (1.64 g, 6.54 mmol) in toluene (20 mL), trimethylaluminum (2M solution in toluene, 3.27 mL, 6.54 mmol) was added over 15 minutes at 0° C. The reaction mixture was warmed to room temperature and stirred for 1 hour. A solution of 2-(isopropyl)-1,3,4-thiadiazole-5-carbonitrile (1 g, 6.54 mmol) in toluene (10 mL) was added over 10 minutes and the reaction mixture was heated to 80–85° C. After 6 hours, the reaction mixture was cooled to room temperature and poured over a slurry of silica gel in chloroformn. After filtration, the residue was washed with a mixture of methylene chloride/methanol (2/1). The combined filtrates were concentrated in vacuo and the residue was titurated with a mixture of hexane/ether (2/1). The resulting solid was collected and dried in vacuo, yield, 2.0 g, 76%; $^1$H NMR δ (DMSO-$d_6$) 7.70 (2H, d, J=8.7 Hz), 7.29 (2H, bs), 7.11 (2H, d, J=8.7 Hz), 5.93 (2H, s), 3.46 (1H, m), 2.36 (6H, s), 1.39 (3H, s), 1.37 (3H, s); $^{13}$C NMR δ (DMSO-$d_6$) 180.1, 166.3, 154.0, 147.5, 132.8, 131.3, 127.7, 122.8, 111.7, 30.2, 22.9, 15.2; MS (m/z): 404.5 (M+, 100%).

EXAMPLE 29

N-[4-(Methylthio)phenyl]-3-[2-(phenyl)-1,3,4-thiadiazol-5-yl]carboximidamide

Following the procedure of Example 24, 2-phenyl-1,3,4-thiadiazole-5-carbonitrile (0.468 g, 2.50 mmol) was added to a mixture of 4-(methylthio)aniline (0.348 g, 2.50 mmol) and trimethylaluminum (2M solution in toluene, 1.25 mL,.2.50 mmol) in toluene (20 mL). The title compound was isolated (0.69 g, 84%) as a light-brown solid; $^1$H NMR δ (DMSO-$d_6$) 8.04 (2H, d, J=7.6 Hz), 7.58 (2H, m), 7.26 (2H, d, J=8.5 Hz), 6.95 (4H, m), 2.46 (3H, s); $^{13}$NMR δ (DMSO-$d_6$) 170.5, 167.5, 146.9, 145.5, 131.7, 131.6, 129.5, 129.4, 127.8, 127.7, 122.4, 15.6.

EXAMPLE 30

N-[4-(Methylthio)phenyl]-3-[2-(4-methylphenyl)-1,3,4-thiadiazol-5-yl]carboximidamide Following the procedure of Example 24, 2-(4-methylphenyl)-1,3,4-thiadiazole-5-carbonitrile (2.01 g, 10 mmol) was added to a mixture of 4-(methylthio)aniline (1.39 g, 10 mmol) and trimethylaluminum (2M solution in toluene, 5 mL, 10 mmol) in toluene (60 mL). The title compound was isolated (2.8 g, 82%) as a light-brown solid; $^1$H NMR δ (DMSO-$d_6$) 7.92 (2H, d, J =7.9 Hz), 7.36 (2H, d, J=8.0 Hz), 7.26 (2H, d, J=8.1 Hz), 6.94 (2H, d, J=8.0 Hz), 2.46 (3H, s), 2.38 (3H, s); $^{13}$C NMR δ (DMSO-$d_6$) 170.6, 167.1, 147.0, 145.5, 141.9, 131.6, 130.0, 127.9, 127.7, 126.7, 122.4, 21.1, 15.6; MS (m/z): 341.3 (M+, 80%).

EXAMPLE 31

N-[4{(2,5-Dimethyl-1H-pyrrol-1-yl)sulfonyl}phenyl]-3-[2-(phenyl)-1,3,4-thiadiazol-5-yl]carboximidamide Following the procedure of Example 28, 2-phenyl-1,3,4-thiadiazole-5-carbonitrile (0.935 g, 5 mmol) was added to a mixture of 1-[(4-aminophenyl)sulfonyl]-2,5-dimethyl-1H-pyrrol (1.25 g, 5 mmol) and trimethylaluminum (2M solution in toluene, 2.5 mL, 5 mmol) in toluene (30 mL). The title compound was isolated (1.76 g, 80%) as a light-brown solid; $^1$H NMR δ (DMSO-$d_6$) 8.04 (2H, d, J=7.5 Hz), 7.71 (2H, d, J=8.7 Hz), 7.59 (4H, m), 7.41 (2H, bs), 7.16 (2H, d, J=8.7 Hz), 5.94 (2H, s), 2.37 (6H, s); $^{13}$C NMR δ (DMSO-$d_6$) 170.9, 166.8, 153.9, 147.5, 132.9, 131.8, 131.3, 129.5, 129.3, 127.9, 127.8, 122.8, 111.7, 15.3, 15.2.

EXAMPLE 32

N-[4-(Aminosulfonyl)phenyl]-3-[2-(phenyl)-1,3,4-thiadiazol-5-yl]carboximidamide

A mixture of N-[4{(2,5-dimethyl-1H-pyrrol-1-yl)sulfonyl}phenyl]-3-[2-(phenyl)-1,3,4-thiadiazol-5-yl]carboximidamide (0.23 g, 0.53 mmol), trifluoroacetic acid (9 mL) and water (3 mL) was refluxed for 1 hour. Trifluoroacetic acid was removed by evaporation in vacuo and the residue was redissolved in ethyl acetate. The organic fraction was washed with aqueous NaHCO$_3$, water, and brine and filtered. The filtrate was concentrated and the resulting crude residue was purified by chromatography (silica gel, hexane/ethyl acetate, 5/5) to give the product (0.11 g, 58%) as a pale yellow solid; $^1$H NMR δ (DMSO-$d_6$) 8.05 (2H, d, J=6.7 Hz), 7.79 (2H, d, J=8.4 Hz), 7.63–7.57 (3H, m), 7.28 (2H, s), 7.23 (2H, bs), 7.11 (2H, d, J=8.2Hz); $^{13}$C NMR δ (DMSO-$d_6$) 170.8, 167.1, 151.4, 147.2, 138.5, 131.8, 129.5, 129.4, 127.9, 127.1, 121.9; MS (m/z): 359.2 (M+, 30%).

EXAMPLE 33

N-[4-(Aminosulfonyl)phenyl]-3-[2-(4-fluorophenyl)-1,3,4-thiadiazol-5-yl]carboximidamide To a suspension of 1-[(4-aminophenyl)sulfonyl]-2,5-dimethyl-1H-pyrrole (1.39 g, 5.55 mmol) in toluene (20 mL), trimethylaluminum (2M solution in toluene, 4.1 mL, 7.77 mmol) was added over 15 minutes at 0° C. The reaction mixture was warmed to room temperature and stirred for 1 hour. A solution of 2-cyano-4-(1-fluorophenyl)-1,3,4-thiadiazole (1.14 g, 5.55 mmol) in toluene (20 mL) was added over 10 minutes and the reaction mixture was heated to 80–85° C. After 6 hours, the reaction mixture was cooled to room temperature and poured over a slurry of silica gel in chloroform. After filtration, the residue was washed with a mixture of methylene chloride/methanol (2/1). The combined filtrates were concentrated in vacuo and the resulting yellowish solid was stirred with a mixture of hexane/ether (2/1). The intermediate was filtered and washed with more hexane/ether (2/1). The pale yellow-brown solid N-[4-{(2,5-dimethyl-1H-pyrrol-1-yl)sulfonyl}phenyl]-2-(1-fluorophenyl)-1,3,4-thiadiazol-5-ylcarboximidamide (2.1 g, 83%) was used in the next reaction without further purification.

A mixture of the product from the preceding paragraph in trifluoroacetic acid (9 mL) and water (3 mL) was refluxed for 1 hour. Trifluoroacetic acid was removed by evaporation in vacuo and the residue was dissolved in ethyl acetate. The organic solution was washed with aqueous $NaHCO_3$, water, and brine and filtered. The filtrate was concentrated and the resulting crude residue was purified by chromatography (silica gel, hexane/ethyl acetate, 5/5) to give the product (1.6 g, 76%) as a pale yellow solid; $^1H$ NMR δ (DMSO-$d_6$) 8.12 (2H, dd, J=8.6, 5.7 Hz), 7.79 (2H, d, J=8.3 Hz), 7.43 (2H, t, J=8.8 Hz), 7.28 (2H, s), 7.11(2H, d, J=8.3 Hz); MS (m/z): 378.5 (M+, 60%).

EXAMPLE 34

N-[4-(Aminosulfonyl)phenyl]-3-[2-(N-anilino)-1,3,4-thiadiazol-5-yl]carboximidamide Following the procedure of Example 33, 2-(N-anilino)-1,3,4-thiadiazole-5-carbonitrile (0.202 g, 1 mmol) was added to a mixture of 1-[(4-aminophenyl)sulfonyl]-2,5-dimethyl-1H-pyrrol (0.25 g, 1 mmol) and trimethylaluminum (2M solution in toluene, 0.7 mL, 1.4 mmol) in toluene (10 mL). The isolated intermediate was dissolved in trifluoroacetic acid (9 mL) and water (3 mL) and heated to reflux for 1 hour. The product was isolated (0.3 g, 66%) as a pale yellow solid; $^1H$ NMR δ (DMSO-$d_6$) 10.7 (1H, bs), 7.76 (2H, d, J=8.3 Hz), 7.64 (2H, d, J=8.0 Hz), 7.38 (2H, m), 7.25 (2H, s), 7.06 (2H, m), 6.90 (1H, s); $^{13}C$ NMR δ (DMSO-$d_6$) 166.7, 156.6, 151.7, 147.7, 140.2, 138.2, 129.2, 127.0, 122.5, 121.9, 117.8; MS (m/z): 374.2 (M+, 100%).

EXAMPLE 35

N-[4-(Aminosulfonyl)phenyl]-3-[2-(methyl)-1,3,4-thiadiazol-5-yl]carboximidamide Following the procedure of Example 33, 2-(methyl)-1,3,4-thiadiazole-5-carbonitrile (0.313 g, 2.5 mmol) was added to a mixture of 1-[(4-aminophenyl)sulfonyl]-2,5-dimethyl-1H-pyrrol (0.626 g, 2.5 mmol) and trimethylaluminum (2M solution in toluene, 1.25 mL, 2.5 mmol) in toluene (10 mL). The isolated intermediate was dissolved in trifluoroacetic acid (9 mL) and water (3 mL) and heated to reflux for 1 hour. The product was isolated (0.5 g, 67%) as a pale yellow solid; $^1H$ NMR δ (DMSO-$d_6$) 7.78 (2H, d, J=8.5 Hz), 7.07 (2H, d, J=7.7 Hz), 2.76 (3H, s); $^{13}C$ NMR δ (DMSO-$d_6$) 168.8, 167.4, 151.5, 147.3, 138.4, 127.0, 121.8, 15.4; MS (m/z): 296.2 (M+, 100%).

EXAMPLE 36

N-[4-(Aminosuifonyl)phenyl]-3-[2-(3,5-di-tert-butyl-4-hydroxyphenyl)-1,3,4-thiadiazol-5-yl]carboximidamide Following the procedure of Example 33, 2-(3,5-di-tert-butyl-4-hydroxyphenyl)-1,3,4-thiadiazole-5-carbonitrile (0.394 g, 1.25 mmol) was added to a mixture of 1-[(4-aminophenyl)sulfonyl]-2,5-dimethyl-1H-pyrrol (0.313 g, 1.25 mmol) and trimethylaluminum (2M solution in toluene, 0.625 mL, 1.25 mmol) in toluene (10 mL). The isolated intermediate was dissolved in trifluoroacetic acid (9 mL) and water (3 mL) and heated to reflux for 1 hour. The product was isolated (0.42 g, 69%) as a pale yellow solid; $^1H$ NMR δ (DMSO-$d_6$) 7.79 (2H, d, J=8.5 Hz), 7.76 (4H, m), 2.27 (2H, s), 7.15 (1H, bs), 7.11 (2H, d, J=8.4 Hz); $^{13}C$ NMR δ (DMSO-$d_6$) 171.6, 165.8, 157.5, 151.5, 147.3, 139.7, 138.4, 127.1, 124.7, 121.8, 120.9, 34.6, 30.0; MS (m/z): 486.5 (M+, 100%).

EXAMPLE 37

1-[4-(Methylthio)phenyl]-2-[2-(methylthio)-1,3,4-thiadiazol-5-yl]-4-(trifluoromethyl)-1H-imidazole To a mixture of N-[4-(Methylthio)phenyl]-3-[2-(methylthio)-1,3,4-thiadiazol-5-yl]carboximidamide (0.69 g, 2.33 mmol) and sodium bicarbonate (0.39 g, 4.66 mmol) in 2-propanol (20 mL) was added 3-bromo-1,1,1-trifluoroacetone (0.62 g, 3.26 mmol). The reaction mixture was heated at 80° C. for 12 hours, cooled to room temperature and concentrated. The crude residue was redissolved in ethyl acetate and washed with water, brine and dried over sodium sulfate, and filtered. The combined organic fractions were concentrated and the crude mixture purified by chromatography on silica gel using hexane/ethyl acetate as an eluent to give 4-hydroxy-1 - [4-(methylthio)phenyl]-2-[2-(methylthio)-1,3,4-thiadiazol-5-yl]-4-(trifluoromethyl)-4,5-dihydro-1H-imidazole (0.52 g, 55%) as a white solid; $^1H$ NMR δ (DMSO-$d_6$) 7.58 (1H, s), 7.22 (2H, d, J=8.6 Hz), 4.42 (1H, d, J=12.2 Hz), 3.88 (1H, d, J=12.1 Hz), 2.78 (3H, s), 2.47 (3H, s); $^{13}C$ NMR δ (DMSO-$d_6$) 171.5, 158.0, 155.0, 136.8, 136.3, 126.3, 125.8, 122.8(q), 94.2(q), 60.9, 16.5, 14.7; MS (m/z): 407.3 (M+, 60%) and dialkylated product (0.6 g, 50%) as a white solid; $^1H$ NMR δ (DMSO-$d_6$) 7.28 (2H, d, J=8.5 Hz), 7.20 (2H, 7.18 (1H, s), 4.68 (1H, s), 4.20 (1H, d, J=10.2 Hz), 4.04 (1H, d, J=10.0 Hz), 2.76 (3H, s); $^{13}C$ NMR δ (DMSO-$d_6$) 172.6, 159.5, 156.9, 138.6, 136.8, 127.9, 126.0, 123.0(q), 121.0(q), 108.0(q), 82.0(q), 76.3, 71.0, 16.6, 14.3; MS (m/z): 517.2 (M+, 40%).

A mixture of 4-hydroxy-1-[4-(methylthio)phenyl]-2-[2-(methylthio)-1,3,4-thiadiazol-5-yl]-4-(trifluoromethyl)-4,5-dihydro-1H-imidazole (0.52 g, 1.28 mmol) and p-toluenesulfonic acid monohydrate (0.1 g) in toluene (20 mL) was heated to reflux for 1 hour. The reaction mixture was cooled to room temperature and the solvent was removed in vacuo. The crude residue was redissolved in ethyl acetate and washed with water, aqueous sodium bicarbonate and brine. After drying ($Na_2SO_4$), filtration, and concentration in vacuo, the crude mixture was purified by chromatography on silica gel using hexane/ethyl acetate to give the title product (0.4 g, 80%) as a white solid; $^1H$ NMR δ (DMSO-$d_6$) 8.38 (1H, s), 7.51 (2H, d, J=8.7 Hz), 7.38 (2H, d, J=8.3 Hz), 2.76 (3H, s), 2.55 (3H, s); $^{13}C$ NMR δ (DMSO-$d_6$) 168.8, 157.4, 140.4, 138.0, 133.0, 131.0(q), 127.2, 126.4, 125.7, 122.0(q), 16.4, 14.4.

EXAMPLE 38

1-[4-(Methysulfonyl)phenyl]-2-[2-(methylsulfonyl)-1,3,4-thiadiazol-5-yl]-4-(trifluoromethyl)-1H-imidazole To a solution of 1-[4-(methylthio)phenyl]-2-[2-(methylthio)-1,3,4-thiadiazol-5-yl]-4-(trifluoromethyl)-1H- imidazole (40 mg, 0.1 mmol) in methylene chloride (6 mL) was added m-chloroperoxybenzoic acid (77% purity, 92 mg, 0.41 mmol). After being stirred for 16 hours, the reaction mixture was diluted with ethyl acetate and washed with saturated aqueous sodium bicarbonate. The combined organic fractions were dried ($Na_2SO_4$), filtered, and concentrated. Chromatography of the crude mixture using hexane/ethyl acetate gave the product (32 mg, 69%) as a white solid; $^1$H NMR δ ($CDCl_3$) 8.10 (2H, d, J=8.3 Hz), 7.68 (2H, d, J=8.3 Hz), 7.64 (1H, s), 3.40 (3H, s), 3.14 (3H, s); $^{13}$C NMR δ ($CDCl_3$) 169.9, 162.9, 142.5, 140.5, 137.2, 135(q), 129.1, 128.0, 125.4, 122.0(q), 44.6, 43.3.

EXAMPLE 39

1-[4-(Methylthio)phenyl]-2-[2-methyl-1,3,4-thiadiazol-5-yl]-4-(trifluoromethyl)-1H-imidazo Following the procedure of Example 37, N-[4-(Methylthio)phenyl]-3-[2-(methyl)-1,3,4-thiadiazol-5-yl] carboximidamide (0.66 g, 2.5 mmol), sodium bicarbonate (0.32 g, 3.75 mmol) in 2-propanol (20 mL) and 3-bromo-1,1,1-trifluoroacetone (0.72 g, 3.75 mmol) give 4-hydroxy-1-[4-(methylthio)phenyl]-2-[2-(methyl)-1,3,4-thiadiazol-5-yl]-4-(trifluoromethyl)-4,5-dihydro-1H-imidazole (0.57 g, 61%) as a white solid; $^1$H NMR δ (DMSO-$d_6$) 7.56 (1H, s), 7.20 (2H, d, J=8.5 Hz), 7.10 (2H, d, J=8.2 Hz), 4.43 (1H, d, J=12.2 Hz), 3.87 (1H, d=12.1 Hz), 2.75 (3H, s), 2.46 (3H, s); $^{13}$C NMR δ (DMSO-$d_6$) 168.5, 158.8, 155.4, 136.8, 136.0, 126.3, 125.5, 122.8(q), 94.0(q), 60.6, 15.1, 14.7; and dialkylated product (0.6 g, 50%) as a white solid; $^1$H NMR δ (DMSO-$d_6$) 7.27 (2H, d, J=8.3 Hz), 7.21 (1H, s), 7.17 (2H, d, J=8.6), 4.69 (1H, s), 4.20 (1H, d, J=10.2 Hz), 4.04 (1H, d, J=10.2 Hz), 2.72 (3H, s), 2.46 (3H, s); $^{13}$NMR δ (DMSO-$d_6$) 169.2, 160.0, 157.7, 138.5, 136.8, 127.7, 126.0, 125.2 (q), 123.0(q), 108.3(q), 81.2(q), 76.1, 71.0, 15.2, 14.3.

A mixture of 4-hydroxy-1-[4-(methylthio)phenyl]-2-[2-(methyl)-1,3,4-thiadiazol-5-yl]-4-(trifluoromethyl)-4,5-dihydro-1H-imidazole (0.15 g, 0.4 mmol) and p-toluenesulfonic acid monohydrate (76 mg) in toluene (20 mL) was heated to reflux for 1 hour. After aqueous work up, the title product (97 mg, 68%) was isolated as a white solid; $^1$H NMR δ ($CDCl_3$) 7.48 (1H, s), 7.28 (4H, s), 2.72 (3H, s), 2.49 (3H, s); $^{13}$C NMR δ ($CDCl_3$) 166.5, 158.6, 141.5, 138.9, 133.2, 1331.1(q), 126.9, 126.4, 124.4, 122.2(q), 15.4.

EXAMPLE 40

1-[4-(Methylsulfonyl)phenyl]-2-[2-methyl-1,3,4-thiadiazol-5-yl]-4-(trifluoromethyl)-1H-imidazole Following the procedure of Example 38, 1-[4-(Methylthio)phenyl]-2-[2-methyl-1,3,4-thiadiazol-5-yl]-4-(trifluoromethyl)-1H-imidazole (0.18 g, 0.51 mmol) and m-chloroperoxybenzoic acid (77% purity, 0.25 g, 1.1 mmol) in methylene chloride (10 mL) give the product (0.15 g, 76%) as a white solid; $^1$H NMR δ (DMSO-$d_6$) 8.50 (1H, s), 8.09 (2H, d, J=8.2 Hz), 7.89 (2H, d, J=8.5 Hz), 3.35 (3H, s), 2.73 (3H, s); $^{13}$C NMR δ (DMSO-$d_6$) 166.7, 158.2, 141.6, 140.6, 138.3, 131.2(q), 127.9, 126.2, 122.4(q), 43.2, 15.0.

EXAMPLE 41

1-[4-(Methylthio)phenyl]-2-(2-isopropyl-1,3,4-thiadiazol-5-yl)-4-(trifluoromethyl)-1-H-imidazole Following the procedure of Example 37, N-[4-(Methylthio)phenyl]-3-[2-(isopropyl)-1,3,4-thiadiazol-5-yl] carboximidamide (1.41 g, 4.83 mmol), sodium bicarbonate (0.81 g, 9.66 mmol) in 2-propanol (72 mL) and 3-bromo-1,1,1-trifluoroacetone (1.38 g, 7.24 mmol) give 4-hydroxy-1-[4-(methylthio)phenyl]-2-[2-(isopropyl)-1,3,4-thiadiazol-5-yl]-4-(trifluoromethyl)-4,5-dihydro-1H-imidazole (0.5 g, 52%) as a white solid; $^1$H NMR δ (DMSO-$d_6$) 7.56 (1H, s), 7.21 (2H, d, J=8.7 Hz), 7.12 (2H, d, J=8.6 Hz), 4.43 (1H, d, J=12.0 Hz), 3.88 (1H, d, J=12.2 Hz), 3.44 (1H, m), 2.47 (3H, s), 1.36 (6H, d, J=6.9 Hz); $^{13}$C NMR δ (DMSO-$d_6$) 179.4, 158.3, 155.4, 136.8, 136.2, 126.3, 125.7, 122.8(q), 94.2(q), 60.8, 30.1, 22.8, 22.7, 14.7; MS (m/z): 403.4 (M+, 90%); and dialkylated product (0.72 g, 58%) as a white solid; $^1$H NMR δ (DMSO-$d_6$) 7.27 (2H, d, J=8.7 Hz), 7.20 (2H, m), 4.70 (1H, s), 4.20 (1H, d, J=10.2 Hz), 4.03 (1H, d, J=10.1 Hz), 3.42 (1H, m), 2.47 (3H, s), 1.32 (6H, d, J=6.9 Hz); $^{13}$C NMR δ (DMSO-$d_6$) 180.2, 159.9, 157.3, 138.6, 136.7, 128.0, 127.7, 125.9, 125.2(q), 122.9, 121.0(q), 108.3(q), 76.3, 71.0, 30.0, 22.9, 22.6, 14.3; MS (m/z): 513.4 (M+, 20%).

A mixture of 4-hydroxy-1-[4-(methylthio)phenyl]-2-[2-(isopropyl)-1,3,4-thiadiazol-5-yl]-4-(trifluoromethyl)-4,5-dihydro-1H-imidazole (0.361 g, 0.90 mmol) and p-toluenesulfonic acid monohydrate (35 mg) in toluene (50 mL) was heated to reflux for 1 hour. After aqueous work up, the product (0.26 g, 75%) was isolated as a white solid; $^1$H NMR δ (DMSO-$d_6$) 8.37 (1H, s), 7.50 (2H, d, J=8.3 Hz), 7.38 (2H, d, J=8.6 Hz), 3.42 (1H, m), 2.55 (3H, s), 1.35 (6H, d, J=6.7 Hz); $^{13}$C NMR δ (DMSO-$d_6$) 177.4, 157.6, 140.3, 138.5, 133.2, 130.9(q), 127.2, 126.4, 125.7, 122.5(q), 29.9, 22.7, 14.4.

EXAMPLE 42

1-[4-(Methylsulfonyl)phenyl]-2-(2-isopropyl-1,3,4-thiadiazol-5-yl)-4-(trifluoromethyl)-1H-imidazole Following the procedure of Example 38, 1-[4-(Methylthio)phenyl]-2-[2-(isopropyl)-1,3,4-thiadiazol-5-yl]-4-(trifluoromethyl)-1H-imidazole (0.12 g, 0.32 mmol) and m-chloroperoxybenzoic acid (77% purity, 0.15 g, 0.69 mmol) in methylene chloride (20 mL) give the product (0.1 g, 77%) as a white solid; $^1$H NMR δ (DMSO-$d_6$) 8.50 (1H, s), 8.10 (2H, d, J=8.7 Hz), 7.91 (2H, d, J=8.7 Hz), 3.34 (1H, m), 3.30 (3H, s), 1.36 (6H, d, J=6.9 Hz); $^{13}$NMR δ (DMSO-$d_6$) 177.6, 157.7, 141.6, 140.6, 138.3, 131.2(q), 128.0, 127.9, 126.3, 122.4(q), 43.2, 29.9, 22.7.

EXAMPLE 43

1-[4-(Methylsulfinyl)phenyl]-2-(2-phenyl-1,3,4-thiadiazol-5-yl)-4-(trifluoromethyl)-1H-imidazole Following the procedure of Example 37, N-[4-(Methylthio)phenyl]-3-[2-(phenyl)-1,3,4-thiadiazol-5-yl] carboximidamide (1.08 g, 3.31 mmol), sodium bicarbonate (0.56 g, 6.62 mmol) in 2-propanol (80 mL) and 3-bromo-1,1,1-trifluoroacetone (0.63 g, 3.31 mmol) give 4-hydroxy-1-[4-(methylthio)phenyl]-2-[2-(phenyl)-1,3,4-thiadiazol-5-yl]-4-(trifluoromethyl)-4,5-dihydro-1H-imidazole (0.5 g, 69%) as a white solid and dialkylated product (0.6 g, 66%) as a white solid; $^1$H NMR δ (DMSO-$d_6$) 8.00 (2H, d, J=7.8 Hz), 7.57 (3H, m), 7.28 (4H, m), 4.74 (1H, s), 4.23 (1H, d, J=10.2 Hz), 4.09 (1H, d, J=10.2 Hz), 3.35 (1H, s), 2.47 (3H, s); $^{13}$NMR δ (DMSO-$d_6$) 171.0, 159.8, 157.5, 138.6, 136.7, 132.3, 129.5, 128.5, 128.2, 127.9, 127.7, 126.0, 125.2(q), 122.5(q), 108.0(q), 81.3(q), 76.4, 71.1, 14.3.

A mixture of 4-hydroxy-1-[4-(methylthio)phenyl]-2-[2-(phenyl)-1,3,4-thiadiazol-5-yl]-4-(trifluoromethyl)-4,5-dihydro-1H-imidazole (0.5 g, 1.15 mmol) and p-toluenesulfonic acid monohydrate (30 mg) in toluene (50 mL) was heated to reflux for 1 hour. After aqueous work up, 1-[4-(Methylthio)phenyl]-2-[2-(phenyl)-1,3,4-thiadiazol-5-yl]-4-(trifluoromethyl)-imidazole was isolated as a white solid.

1-[4-(Methylthio)phenyl]-2-[2-(phenyl)-1,3,4-thiadiazol-5-yl]-4-(trifluoromethyl)-1H-imidazole (0.39 g, 0.93 mmol) and m-chloroperoxybenzoic acid (77% purity, 0.21 g, 0.93 mmol) in methylene chloride (20 mL) give the product (0.31 g, 77%) as a white solid; $^1$H NMR δ (DMSO-$d_6$) 8.52 (1H, s), 8.00 (2H, d, J=7.2 Hz), 7.88 (4H, s), 7.56 (3H, m), 2.86 (3H, s); $^{13}$C NMR δ (DMSO-$d_6$) 168.7, 158.0, 147.7, 138.2, 138.1, 131.9, 131.3(q), 129.5, 128.9, 127.9, 127.8, 126.6, 124.6, 122.4(q), 43.0.

EXAMPLE 44

1-[4-(Methylsulfonyl)phenyl]-2-(2-phenyl-1,3,4-thiadiazol-5-yl)-4-(trifluoromethyl)-1H-imidazole Following the procedure of Example 38, 1-[4-(methylthio)phenyl]-2-[2-(phenyl)-1,3,4-thiadiazol-5-yl]-4-(trifluoromethyl)-1H-imidazole (0.26 g, 0.63 mmol) and m-chloroperoxybenzoic acid (77% purity, 0.34 g, 1.5 mmol) in methylene chloride (20 mL) give the product (0.21 g, 75%) as a white solid; $^1$H NMR δ (DMSO-$d_6$) 8.55 (1H, s), 8.13 (2H, d, J=8.5 Hz), 8.01 (2H, d, J=7.3 Hz), 7.97 (2H, d, J=8.2 Hz), 7.58 (3H, m), 3.37 (3H, s); $^{13}$NMR δ (DMSO-$d_6$) 168.7, 158.0, 141.7, 140.5, 138.1, 131.9, 131.7(q), 129.6, 128.8, 128.0, 127.9, 127.8, 126.5, 122.0(q), 43.2.

EXAMPLE 45

1-[4-(Methylsulfonyl)phenyl]-2-(1,4-biphenyl)-4-(trifluoromethyl)-1H-imidazole Following the procedure of Example 37, N-[4-(methylthio)phenyl]-3-(1,4-biphenyl)-carboximidamide (1.06 g, 3.33 mmol), sodium bicarbonate (0.56 g, 6.66 mmol) in 2-propanol (80 mL) and 3-bromo-1,1,1-trifluoroacetone (0.95 g, 4.99 mmol) give 4-hydroxy-1-[4-(methylthio)phenyl]-2-(1,4-diphenyl)-4-(trifluoromethyl)-4,5-dihydro-1H-imidazole (1.02 g, 72%) as a white solid.

A mixture of 4-hydroxy-1-[4-(methylthio)phenyl]-2-(1,4-diphenyl)-4-(trifluoromethyl)-4,5-dihydro-1H-imidazole (1.02 g, 2.38 mmol) and p-toluenesulfonic acid monohydrate (50 mg) in toluene (50 mL) was heated to reflux for 1 hour. After aqueous work up, 1-[4-(Methylthio)phenyl]-2-(1,4-diphenyl)-4-(trifluoromethyl)-1H-imidazole was isolated as a white solid.

1-[4-(Methylthio)phenyl]-2-(1,4-diphenyl)-4-(trifluoromethyl)-1H-imidazole (0.8 g, 1.95 mmol) and m-chloroperoxybenzoic acid (77% purity, 1.05 g, 4.68 mmol) in methylene chloride (50 mL) give the product (0.69 g, 80%) as a white solid; $^1$H NMR δ (DMSO-$d_6$) 8.36 (1H, s), 8.08 (2H, d, J=8.6 Hz), 7.74 (2H, d, J=8.7 Hz), 7.69 (4H, m), 7.46 (4H, t, J=7.6 Hz), 7.38 (1H, t, J=7.1 Hz), 3.31 (3H, s); $^{13}$C NMR δ (DMSO-$d_6$) 147.1, 141.1, 141.0 140.9, 138.8, 130.9(q), 129.3, 129.0, 128.5, 128.0, 127.6, 127.3, 126.7, 124.1, 122.0(q), 43.2.

EXAMPLE 46

1-[4-(Methylsulfonyl)phenyl]-2-[2-(4-methylphenyl)-1,3,4-thiadiazol-5-yl]-4-(trifluoromethyl)-1H-imidazole Following the procedure of Examples 37 and 38, the title compound was isolated (69% yield) as a white solid; $^1$H NMR δ (DMSO-$d_6$) 8.54 (1H, s), 8.12 (2H, d, J=8.3 Hz), 7.96 (2H, d, J=8.6 Hz), 7.89 (2H, d, J=8.4 Hz), 7.36 (2H, d, J=8.1 Hz), 3.38 (3H, s); $^{13}$NMR δ (DMSO-$d_6$) 168.8, 157.5, 142.1, 141.7, 140.6, 138.2, 131.4, 130.1, 128.0, 127.9, 127.8, 126.2, 126.2, 121.1, 43.2, 21.0; MS (m/z): 464.5 (M+, 60%).

EXAMPLE 47

1-[4-{(2-Trimethyl silyl) ethyl)sulfonyl}phenyl]-2-[2-(phenyl)-1,3,4-thiadiazol-5-yl]-4-(trifluoromethyl)-1H-imidazole To diisopropylamine (1.03 g, 10.2 mmol) in dry THF (60 mL) at 0° C. was added nBuLi (5.75 mL, 1.6 M in hexane, 9.2 mmol). The solution was stirred for 10 min and then cooled to −78° C. with dry ice/acetone bath. A solution of 1-[4-(methylsulfonyl)phenyl]-2-(2-phenyl-1,3,4-thiadiazol-5-yl)-4-(trifluoromethyl)-1H-imidazole (2.30 g, 5.11 mmol) in dry THF (30 mL) was added over 10 min and the reaction mixture stirred for 1 hour. (Iodomethyl)trimethylsilane (2.19 g, 10.2 mmol) was added dropwise and the mixture stirred overnight while allowed to warm to room temperature. The reaction mixture was quenched with 1N HCl (20 mL) and the aqueous phase extracted with ethyl acetate (3×60 mL). The combined organic fractions were washed with brine, dried (Na$_2$SO$_4$) and concentrated. The residue was purified by chromatography on silica gel using hexane/ethyl acetate as an eluent to give the product (2.2 g, 80%) as a white solid; $^1$H NMR δ (CDCl$_3$) 8.05 (2H, d, J=8.2 Hz), 7.91 (2H, d, J=8.8 Hz), 7.69 (2H, d, J=8.3 Hz), 7.59 (1H, s), 7.48 (3H, m), 3.08 (2H, m), 1.03 (2H, m), 0.06 (9H, s); $^{13}$C NMR δ (CDCl$_3$) 170.0, 157.9, 141.0, 140.6, 138.7, 134.3(q), 132.0, 129.8, 129.5, 129.4, 128.2, 127.8, 124.4(q), 53.1, 8.9, −1.8.

EXAMPLE 48

1-[4-(Aminosulfonyl)phenyl]-2-[2-(phenyl)-1,3,4-thiadiazol-5-yl]-4-(trifluoromethyl)-1H-imidazole To a solution of 1-[4- {(2-trimethyl silyl) ethyl) sulfonyl}phenyl]-2-[2-(phenyl)-1,3,4-thiadiazol-5-yl]-4-(trifluoromethyl)-1H-imidazole (2.3 g, 4.29 mmol) in dry THF (50 mL) was added tetrabutylammonium fluoride (12.8 mL, 1M solution in THF, 12.8 mmol). The mixture was refluxed for 30 min and cooled to room temperature. A solution of sodium acetate trihydrate (2.92 g, 21.4 mmol) in water (5 mL) was added followed by hydroxylamine-O-sulfonic acid (2.42 g, 21.4 mmol), and the mixture was stirred for 4 hour. The reaction mixture was quenched by adding water (50 mL) and extracted with ethyl acetate. The organic fractions were washed with water, brine, dried (Na$_2$SO$_4$) and evaporated in vacuo. The residue was purified by chromatography on silica gel using hexane/ethyl acetate as an eluent to give the product (1.2 g, 62%) as a white solid; $^1$H NMR δ (DMSO-$d_6$) 8.54 (1H, s), 7.98 (4H, m), 7.87 (2H, d, J=8.7 Hz), 7.61 (2H, s), 7.58 (3H, m); $^{13}$C NMR δ (DMSO-$d_6$) 170.7, 160.0, 147.0, 141.0, 140.1, 133.9, 133.7, 131.6, 130.9, 129.9, 129.6, 128.6, 124.0(q).

EXAMPLE 49

1-[4-(Methylsulfonyl)phenyl]-2-[2-(4-fluorophenyl)-1,3,4-thiadiazol-5-yl]-4-(trifluoromethyl)-1H-imidazole A mixture of 4-(trifluoromethyl)-1H-imidazole [*Indian J. Chem.*, Sect. B, 1988, 27B(11), 1051–3] (1.94 g, 14.3 mmol), 4-fluoro methyl phenyl sulfone (2.48 g, 14.3 mmol sodium carbonate (3.02 g, 28.5 mmol) in DMF (20 mL) was heated at 120° C. for 24 hours. The reaction mixture was cooled to room temperature and diluted with ethyl acetate and washed with water and brine. The combined organic fraction was dried ($Na_2SO_4$) and evaporated to dryness. The crude product was purified by chromatography on silica gel using hexane/ethyl acetate as an eluent to give 1-[4-(methylsulfonyl)phenyl]-4-(trifluoromethyl)-1H-imidazole (3.6 g, 87%) as a white solid; $^1$H NMR δ (DMSO-$d_6$) 8.64 (1 H, s), 8.62 (1H, s), 8.10 (2H, d, J=8.8 Hz), 8.05 (2H, d, J=8.8 Hz), 7.85 (1H, s), 7.75 (1H, s), 3.30 (3H, s); $^{13}$C NMR δ (DMSO-$d_6$) 139.8, 139.7, 137.8, 137.3, 128.9, 121.5, 119.3, 117.5, 43.4.

To a solution of 1-[4-(methylsulfonyl)phenyl]-4-(trifluoromethyl)-1H-imidazole (2.02 g, 6.96 mmol) in dry THF (10 mL) was added nBuLi (10.4 mL, 1.6 M in hexane, 16.7 mmol) at −78° C. The reaction mixture was stirred for 4 hours and quenched with DMF (2.04 g, 27.8 mmol) and stirred for 1 hour with temperature rising to room temperature. The mixture was diluted with ethyl acetate and washed with water, brine and dried. The combined organic fraction was evaporated and the residue was purified by chromatography on silica gel using hexane/ethyl acetate as an eluent to give the aldehyde (1.6 g, 72%) as a white solid; $^1$H NMR δ (DMSO-$d_6$) 9.74 (1H, s), 8.58 (1H, s), 8.11 (2H, d, J=8.1 Hz), 7.90 (2H, d, J=8.7 Hz), 3.34 (3H, s); $^{13}$C NMR δ (DMSO-$d_6$) 180.6, 143.1, 141.6, 139.8, 131.8(q), 128.0, 127.3, 120.1(q), 43.2.

The above aldehyde (0.2 g, 0.628 mmol) and 4-fluorophenylthiohydrazide [*J. Prakt. Chem.*, 1989, 331(4), 649–58] in ethanol (10 mL) was heated to reflux for 1 hour. The reaction mixture was cooled to room temperature and DDQ (0.2 g, 0.879 mmol) was added and stirred for 6 hours. The mixture was diluted with ethyl acetate and washed with aqueous sodium bicarbonate, water, brine and dried. The combined organic fractions were evaporated to dryness and the residue was purified by chromatography on silica gel using hexane/ethyl acetate as an eluent to give the product (0.12 g, 41%) as a pale yellow solid; $^1$H NMR δ (DMSO-$d_6$) 8.54 (1H, s), 8.13 (2H, m), 8.08 (2H, dd, J=8.7, 5.8 Hz), 7.96 (2H, m), 7.41 (2H, m), 3.36 (3H, s); $^{13}$C NMR δ (DMSO-$d_6$) 167.6, 165.1, 163.1, 158.1, 141.7, 140.5, 138.0, 131.4(q), 130.4, 130.3, 128.0, 127.9, 126.5, 125.5, 121.0(q), 116.8, 116.6, 43.2; MS (m/z): 469.4 (M+, 10%).

EXAMPLE 50

1-[4-(Methylsulfonyl)phenyl]-2-[2-(phenyl)-1,3,4-thiadiazol-5-yl]-1H-imidazole

2-Imidazolecarboxaldehyde (0.3 g, 3.12 mmol) and phenylthiohydrazide [*J. Prakt. Chem.*, 1989, 331(4), 649–58] in ethanol (12 mL) was heated to reflux for 1 hour. The reaction mixture was cooled to room temperature and DDQ (0.2 g, 0.879 mmol) was added and stirred for 6 hours. The mixture was diluted with ethyl acetate and washed with aqueous sodium bicarbonate, water, brine and dried. The combined organic fractions were evaporated to dryness and the residue was purified by chromatography on silica gel using hexane/ethyl acetate as an eluent to give 2-[2-(phenyl)-1,3,4-thiadiazol-5-yl]-H-imidazole (0.43 g, 60%) as a pale yellow solid.

A mixture of 2-[2-(phenyl)-1,3,4-thiadiazol-5-yl]-1H-imidazole (0.143 g, 0.63 mmol), 4-fluoro methyl phenyl sulfone (0.11 g, 0.63 mmol) and sodium carbonate (0.132 g, 1.25 mmol) in DMF (10 mL) was heated at 120° C. for 24 hours. The reaction mixture was cooled to room temperature and diluted with ethyl acetate and washed with water and brine. The combined organic fraction was dried ($Na_2SO_4$) and evaporated to dryness. The crude product was purified by chromatography on silica gel using hexane/ethyl acetate as an eluant to give the product (0.19 g, 79%) as a white solid; $^1$H NMR δ (DMSO-$d_6$) 8.10 (2H, d, J=6.9 Hz), 7.98 (2H, d, J=7.6 Hz), 7.86 (2H, d, J=7.2 Hz), 7.79 (1H, s), 7.55 (3H, m), 7.43 (1H, s), 3.36 (3H, s); $^{13}$C NMR δ (DMSO-$d_6$) 167.8, 159.1, 141.4, 141.0, 136.6, 131.6, 130.9, 129.5, 129.1, 127.9, 127.8, 127.6, 126.4, 43.3.

EXAMPLE 51

1-[4-Nitrophenyl]-2-[2-(phenyl)-1,3,4-thiadiazol-5-yl]-1H-imidazole

A mixture of 2-[2-(phenyl)-1,3,4-thiadiazol-5-yl]-1H-imidazole (0.285 g, 1.25 mmol), 1-fluoro-4-nitrobenzene (0.176 g, 1.25 mmol) and sodium carbonate (0.265 g, 2.50 mmol) in DMF (10 mL) was heated at 120° C. for 24 hours. The reaction mixture was cooled to room temperature and diluted with ethyl acetate and washed with water and brine. The combined organic fraction was dried ($Na_2SO_4$) and evaporated to dryness. The crude product was purified by chromatography on silica gel using hexane/ethyl acetate as an eluant to give the product (0.38 g, 87%) as a white solid; $^1$H NMR δ (DMSO-$d_6$) 8.38 (2H, d, J=8.9 Hz), 7.98 (2H, dd, J=7.7, 1.6 Hz), 7.86 (2H, dd, J=8.8, 1.6 Hz), 7.81 (1H, s), 7.55 (3H, m), 7.43 (1H, dd, J=1.3 Hz); $^{13}$C NMR δ (DMSO-$d_6$) 167.8, 159.1, 147.3, 142.6, 136.6, 131.6, 131.0, 129.5, 129.0, 128.1, 127.7, 126.2, 124.3; MS (m/z): 350.4 (M+, 100%).

EXAMPLE 52

1-[4-(Methylsulfonyl)phenyl]-2-[2-(N-anilino)-1,3,4-thiadiazol-5-yl]-4-(trifluoromethyl)-1H-imidazole A mixture of 1-[4-(methylsulfonyl)phenyl]-4-(trifluoromethyl)-2-imidazolecarboxaldehyde (0.398 g, 1.25 mmol) and 4-phenyl-3-thiosemicarbazide (0.23 g, 1.25 mmol) in ethanol (10 mL) was heated to reflux for 2 hours. The reaction mixture was cooled to room temperature and DDQ (0.568 g, 2.50 mmol) was added and stirred for 6 hours. The mixture was diluted with ethyl acetate and washed with aqueous sodium bicarbonate, water, brine and dried. The combined organic fractions were evaporated to dryness and the residue was purified by chromatography on silica gel using hexane/ethyl acetate as an eluant to give the product (0.4 g, 69%) as a pale yellow solid; $^1$H NMR δ (DMSO-$d_6$) 10.7 (1H, s), 8.42 (1H, s), 8.12 (2H, d, J=8.7 Hz), 7.92 (2H, d, J=8.1 Hz), 7.59 (2H, d, J=8.2 Hz), 7.34 (2H, t, J=7.5 Hz), 7.02 (1H, t, J=7.7 Hz), 3.36 (3H, s); $^{13}$C NMR δ (DMSO-$d_6$) 164.9, 147.8, 141.5, 140.7, 140.0, 138.6, 130.8, 129.1, 127.9, 127.8, 125.8, 122.5, 117.8, 43.3; MS (m/z): 466.6 (M+, 100%).

Example 53 describes the in vitro inhibition of COX-2 by a variety of invention compounds

EXAMPLE 53

Assay for COX-1 and COX-2 activity (Ovine)

COX activity was assayed as $PGE_2$ formed/μg protein/time using ELISA to detect prostaglandin release. CHAPS-solubilized insect cell membranes containing the appropriate COX enzyme were incubated in a potassium phosphate buffer (50 mM, pH 8.0) containing Tris-HCl, EDTA, phenol, and heme with the addition of arachidonic acid (10 μM). Compounds were pre-incubated with the enzyme for 5–10 minutes prior to the addition of arachidonic acid. Any reaction between the arachidonic acid and the enzyme was stopped after two minutes at 37° C. The $PGE_2$ formed was measured by standard ELISA technology (Cayman Chemical). Results are shown in Table 1.

TABLE 1

| Example | COX-1 10 nM (% inhibition) | COX-1 50 nM (% inhibition) | COX-2 10 nM (% inhibition) | COX-2 50 nM (% inhibition) | IC50 COX1 (nM)/COX2 (nM) | Selectivity |
|---|---|---|---|---|---|---|
| Celecoxib | 50 | 64 | 90 | 99 | 9.6/3.4 | 4 |
| Valdecoxib | 2 | | 71 | | 84.6/0.6 | 141 |
| 29(MX1348) | 15 | 45 | 85 | 94 | 79.0/4.8 | 17 |
| 30(MX1365) | 23 | 52 | 84 | 100 | 36.0/3.3 | 11 |
| 31 | 0 | 15 | 77 | 86 | 77.0/3.9 | 20 |
| 32 | 19 | 40 | 30 | 45 | | |
| 33 | 22 | 75 | 20 | 24 | | |
| 39 | 44 | 55 | 95 | 98 | | |
| 40 | 37 | | 94 | | | |
| 41(MX1265) | 30 | 45 | 95 | 100 | 27.0/2.3 | 12 |
| 42 | 23 | 79 | 26 | | | |
| 45(MX1297) | 10 | 25 | 84 | 100 | 36.0/0.4 | 90 |
| 46 | 64 | | 75 | | | |
| 47 | 39 | | 89 | | | |
| 48 | 43 | | 85 | | 40.0/4.8 | 8 |
| 49(MX1363) | 31 | | 98 | | 62.0/5.1 | 12 |

As shown in Table 1, invention compounds exhibit a marked selectivity for the inhibition of COX-2 over COX-1.

Example 54 describes and illustrates the pharmacokinetic data in rats for some exemplary invention compounds.

EXAMPLE 54

The animals are housed, fed and cared for according to the Guidelines of the American Council on Animal Care. Male Sprague Dawley rats (250–300 g) are fasted overnight prior to each PO blood level study. The rats are placed in the restrainer one at a time and the box firmly secured. Compounds are prepared as required, in a standard dosing volume of 500 µL/250 g, and administered orally by passing a 16 gauge, 3" gavaging needle into the stomach. Rats are catheterized at the carotid at least one day before drug administration and flushed with 30% PVP (400 U/mL of heparin) to prevent clotting in the tip. 250 µL blood samples are collected by unhooking the flush syringe and letting the blood flow freely in centrifuge tube at predetermined time points. The tubes should be centrifuged at 13,000 rpm for 10 min at 4° C. The plasma samples are collected in microcentrifuge tubes and stored immediately at –20° C. until analysis or analyzed immediately. Typical time points for determination of rat blood levels after PO dosing are: 30 min, 1 h, 3 h, 5 h, 7 h, 23 h, 25 h, 28 h, 31 h. A 100 µL aliquot of plasma sample is mixed with 150 µL of acetonitrile. After vortex and centrifuge, 200 µL of the supernatant is dried up under Speed Vac. The residue is reconstituted with 100 µL of methanol. After vortex and centrifuge again, 25 µL of supernatant is analyzed by C-18 HPLC column using UV detector. Quantitation is done relative to a clean blood sample spiked with a known quantity of drug. Bioavailability (F) is assessed by comparing area under the curve (AUC) i.v. versus p.o. (see FIGS. 1 and 2).

Figure 2:
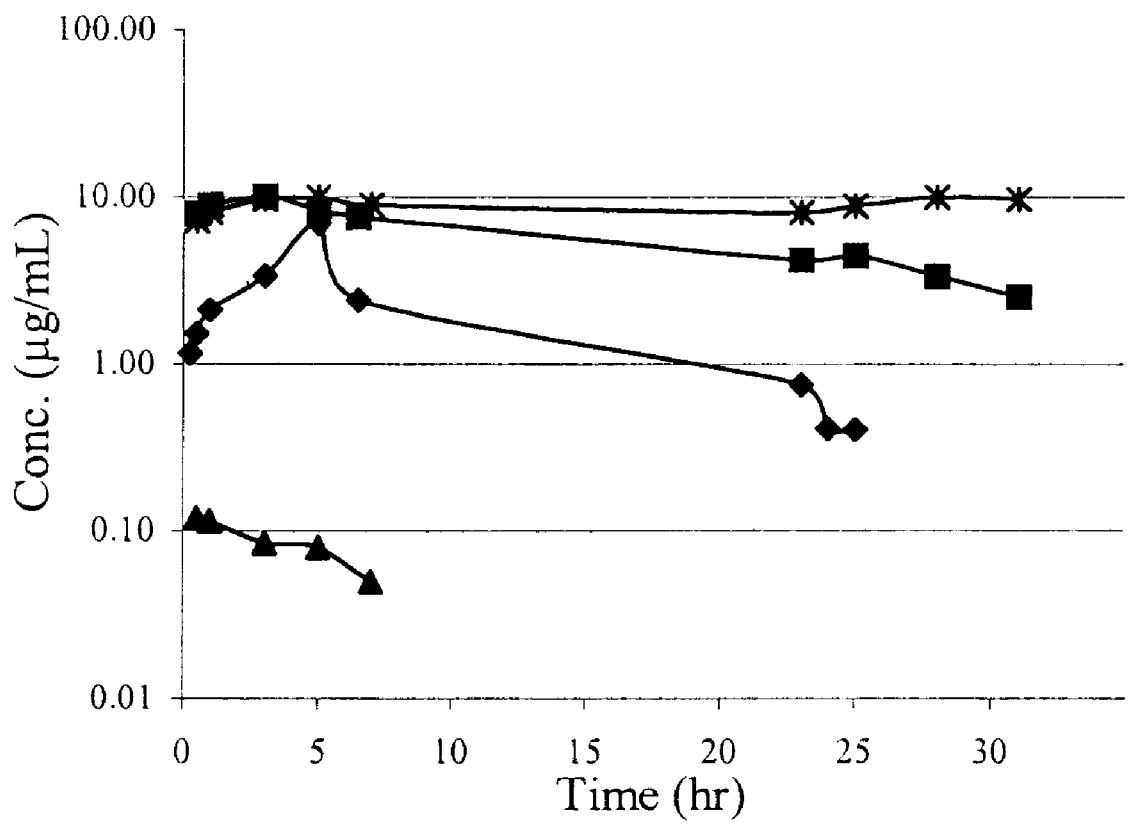
FIG. 2 illustrates pharmacokinetic data for Celecoxib™ (♦), invention compound Example 32 (MX-1348) (■), invention compound Example 52 (MX-1363) (▼), and invention compound Example 33 (MX-1365) (*) after oral administration in rats.

Compounds which exhibit a marked selectivity for the inhibition of COX-2 over COX-1 were examined in the rat to assess their pharmacokinetics (FIGS. 1 and 2). Referring to FIG. 2, Example 48 (MX-1297) (♦), Example 32 (MX-1348) (■) and Example 33 (MX-1365) (*) demonstrated a similar pharmacology profile to Celecoxib™ (●) but with a longer half-life.

Example 55 describes and illustrates the percentage inhibition of paw swelling in rats by invention compounds, wherein the paw swelling results from adjuvant-induced arthritis.

EXAMPLE 55

Male Lewis rats (175–199 g) were obtained from Harlan. Animals were allowed to acclimatize to the facility for a minimum of 3 days and provided food and water ad libitium. Mycobacterium tuberculosis (Difco, Bacto H37 RA 3114-25) was dissolved in mineral oil (5 mg/ml) and arthritis induced by injecting 100 µl of the solution into the left footpad using a 25G needle. Paw volume was measured using a water plethysmometer (UBS Basile, Stoelting Co.) A line was drawn across the right ankle to provide the level for baseline measurement of paw volume and paw volume measured on days 0, 5, 11, 13 and 15. The percentage inhibition of paw volume swelling produced for each treatment was calculated for day 15. Celecoxib was formulated in polyethyleneglycol, and dosed at 5ml/kg, and inhibitors were formulated in polyethyleneglycol (MW. 300; Sigma Chemical Co., St. Louis, Mo.), and dosed at 1 ml/kg. Drug and vehicle were administered orally, daily, on days 8–15.

Figure 3:
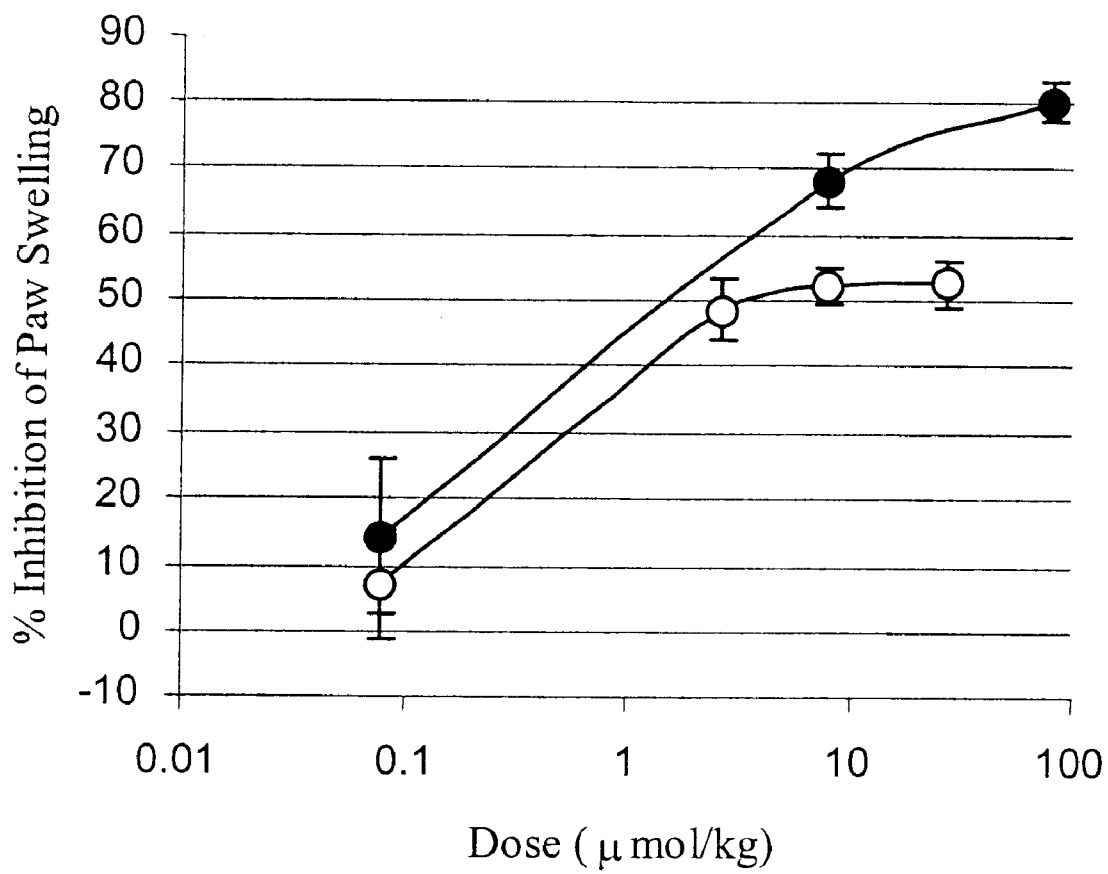
FIG. 3 illustrates percentage inhibition of paw swelling in adjuvant-induced arthritis in rats for Celecoxib™ (●) and invention compound Example 48 (MX-1297) (○).

Compound, Example 48 (MX-1297) (♦) which exhibits good selectivity for the inhibition of COX-2 over COX-1 and shows excellent pharmacology profile was evaluated in the adjuvant-induced arthritis rat model (FIG. 3). Example 48 shows good potency in controlling inflamation.

While the invention has been described in detail with reference to certain prefered embodiments thereof, it will be understood that modifications and variations are within the spirit and scope of that which is described and claimed.

What is claimed is:

1. A compound having the structure:

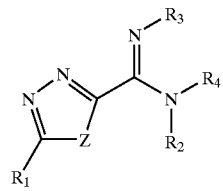

wherein:
Z is O or S,
$R_1$ is optionally substituted aryl,
$R_2$ is aryl optionally substituted with aminosulfonyl, and
$R_3$ and $R_4$ cooperate to form an optionally substituted 5-membered ring.

2. A compound according to claim 1 wherein said optionally substituted aryl is phenyl, naphthyl, or biphenyl.

3. A compound according to claim 2, wherein said optionally substituted aryl is phenyl.

4. A compound according to claim 1, wherein said substituents on $R_1$ are independently one or more of hydroxyl, halogen, cyano, nitro, carboxyl, optionally substituted allyl, aryl, alkoxy, thioalkyl, amino, alkylamino, arylamnino, aminosulfonyl, alkylsulfonyl, or alkoxycarbonyl.

5. A compound according to claim 4 wherein said substituents on $R_1$ are independently one or more of halogen, haloalkyl, alkyl, alkoxycarbonyl, alkylsulfonyl, or aminosulfonyl.

6. A compound according to claim 1, wherein said 5-membered ring is optionally substituted with one or more of hydroxy, halogen, optionally substituted alkyl, aryl, aralkyl, heteroaryl, heterocyclic, alkoxy, aryloxy, thioalkyl, thioaryl, acyl, cyano, sulfonyl, alkylsulfonyl, alkylcarbonyl, arylcarbonyl, amino, carboxyl, or aminocarbonyl.

7. A compound according to claim 6, wherein said substituents are one or more of lower alkyl, haloalkyl, halogen, lower alkoxy, lower thioalkyl, heteroaryl, or heterocyclic.

8. A pharmaceutical composition comprising a compound according to claim 1 in a pharmaceutically acceptable carrier therefor.

9. A composition according to claim 8 wherein said pharmaceutically acceptable carrier is a solid, solution, emulsion, dispersion, micelle, or liposome.

10. A composition according to claim 9 wherein said pharmaceutically acceptable carrier further comprises an enteric coating.

11. A method for treating inflammation and inflammation-related conditions, said method comprising administering to a subject in need thereof an effective amount of a compound according to claim 1.

12. A method according to claim 11, wherein said inflammation-related condition is arthritis.

13. A method according to claim 12, wherein said arthritis is rheumatoid arthritis, gouty arthritis, osteoarthritis, juvenile arthritis, systemic lupus erythematosus, or spondyloarthopathies.

14. A method according to claim 11, wherein said inflammation-related condition is a gastrointestinal condition, headache, asthma, bronchitis, menstrual cramps, tendinitis, or bursitis.

15. A method according to claim 14, wherein said inflammation-related condition is a gastrointestinal condition.

16. A method according to claim 15, wherein said gastrointestinal condition is inflammatory bowel disease, Crohn's disease, gastritis, irritable bowel syndrome, or ulcerative colitis.

17. A method according to claim 11, wherein said inflammation-related condition is headache.

18. A method according to claim 17, wherein said headache is migraine.

19. A method according to claim 11 wherein said inflammation-related condition is associated with vascular diseases, periarteritis nodosa, thyroidiris, aplastic anemia, Hodgkin's disease, sclerodoma, rheumatic fever, type I diabetes, myasthenia gravis, colorectal cancer, sarcoidosis, nephrotic syndrome, Behcet's syndrome, potymyositis, gingivitis, hypersensitivity, conjunctivitis, swelling occurring after injury, or myocardial ischemia.

20. A method according to claim 11 wherein said subject is a mammal.

21. A method according to claim 20 wherein said mammal is human.

22. A method for treating psoriasis, eczema, burn, or dermatitis, said method comprising administering to a subject in need thereof an effective amount of a compound according to claim 1.

23. A method for reducing side effects associated with administration of anti-inflammatory agents to a subject in need thereof, said method comprising administering to said subject an effective amount of a compound according to claim 1.

24. A method for selectively inhibiting COX-2 in the presence of COX-1, said method comprising administering to a subject in need thereof an effective amount of a compound according to claim 1.

* * * * *

UNITED STATES PATENT AND TRADEMARK OFFICE
CERTIFICATE OF CORRECTION

PATENT NO. : 6,555,563 B1  
DATED : April 29, 2003  
INVENTOR(S) : Van-Duc Le and Jean-Frederick Salazar It is certified that error appears in the above-identified patent and that said Letters Patent is hereby corrected as shown below:

Column 29,  
Line 7, change "allyl" to -- alkyl --  
Line 8, change "arylamnino" to -- arylamino --

Signed and Sealed this

Ninth Day of September, 2003

JAMES E. ROGAN  
*Director of the United States Patent and Trademark Office*